US007863014B2

(12) United States Patent
Kawai et al.

(10) Patent No.: US 7,863,014 B2
(45) Date of Patent: Jan. 4, 2011

(54) PROCESS FOR PREPARING NICOTINAMIDE ADENINE DINUCLEOTIDE PHOSPHATE(NADP)

(75) Inventors: Shigeyuki Kawai, Kyoto (JP); Kousaku Murata, Kyoto (JP); Hirokazu Matsukawa, Tokyo (JP); Shoichi Tomisako, Tokyo (JP); Yoshio Ando, Tokyo (JP); Yuhsi Matsuo, Tokyo (JP)

(73) Assignee: Oriental Yeast Co., Ltd., Tokyo (JP)

( * ) Notice: Subject to any disclaimer, the term of this patent is extended or adjusted under 35 U.S.C. 154(b) by 516 days.

(21) Appl. No.: 10/482,791

(22) PCT Filed: Jul. 2, 2002

(86) PCT No.: PCT/JP02/06692

§ 371 (c)(1), (2), (4) Date: Jul. 20, 2004

(87) PCT Pub. No.: WO03/004654

PCT Pub. Date: Jan. 16, 2003

(65) Prior Publication Data

US 2004/0248263 A1 Dec. 9, 2004

(30) Foreign Application Priority Data

Jul. 2, 2001 (JP) .............................. 2001-201400

(51) Int. Cl.
*C12P 1/00* (2006.01)
(52) U.S. Cl. ....................................................... 435/41
(58) Field of Classification Search .................... 435/90
See application file for complete search history.

(56) References Cited

FOREIGN PATENT DOCUMENTS

JP 52-82792 7/1977

OTHER PUBLICATIONS

Kawai et al., Biochem. Biophys. Res. Commun. 2000, vol. 276, No. 1, p. 57-63.*
Ngo et al. in The Protein Folding Problem and Tertiary Structure Prediction, 1994, Merz et al. (ed.), Birkhauser, Boston, MA, pp. 433 and 492-495, Ref: U, Form-892.*
Zerez et al, Negative modulation of *Escherichia coli* NAD kinase by NADPH and NADH. J Bacteriol. Jan. 1987;169(1):184-8.*
USPTO in house BLAST alignment of SEQ ID No. 1 with PIR database F70502 and UniProt database P0A5S6.*
Labesse et al, Diacylglyceride kinases, sphingosine kinases and NAD kinases: distant relatives of 6-phosphofructokinases. Trends Biochem Sci. Jun. 2002;27(6):273-5. Review.*
Kawai et al, "Establishment of Mass-Production System for NADP Using Bacterial Inorganic Polyphosphate/ATP-NAD Kinase", J. Biosci. Bioeng., Dec. 2001, vol. 92, No. 5, pp. 447-452.
Kawai et al, "Inorganic Polyphosphate/ATP-NAD Kinase of *Micrococcus flavus* and *Mycobacterium tuberculosis* H37Rv", Biochem. Biophys. Res. Commun. 2000, vol. 276, No. 1, pp. 57-63.
Beutler et al, "Coenzymes, metabolites, and other biochemical reagents", pp. 328-393, In Bergmeyer, H. U. (ed.), Methods of enzymatic analysis, vol. 1, Verlag Chemie, Weinheim (1983).
Matsushita et al, "NADP production using thermostable NAD kinase of *Corynebacterium flaccumfaciens* AHU-1622", Can. J. Microbiol., vol. 32, 1986, pp, 585-590.
McGuinness et al, "NAD Kinase—A Review", Int. J. Biochem., vol. 17, No. 1, pp. 1-11, 1985.
Murata et al, "Continuous Production of NADP by Immobilized *Brevibacterium ammoniagenes* Cells", Biotechnology and Bioengineering, vol. XXI, pp. 887-895 (1979).
Murata et al, "Metaphosphate: A New Phosphoryl Donor for NAD Phosphorylation", Agric. Biol. Chem., 44(1), 61-68, 1980.
Wood et al, "Biological Aspects of Inorganic Polyphosphates", Ann. Rev. Biochem. 1988, 57:235-260.
Kawai et al, "Inorganic Polyphosphate/ATP-NAD Kinase of *Micrococcus flavus* and *Mycobacterium tuberculosis* H37Rv", Biochemical and Biophysical Research Communications, 276, 57-63 (2000).
Ausubel et al, "Current Protocols in Molecular Biology", John Wiley & Sons, Inc., New York (1994).
Bradford et al, "A Rapid and Sensitive Method for the Quantitation of Microgram Quantities of Protein Utilizing the Principle of Protein-Dye Binding", Analytical Biochemistry 72, 248-254 (1976).
Chibata et al, "Immobilized Aspartase-Containing Microbial Cells: Preparation and Enzymatic Properties", Applied Microbiology, May 1974, vol. 27, No. 5, pp. 878-885.
Murata et al, "Continuous Production of Glucose-6-phosphate by Immobilized *Achromobacter butyri* Cells", European J. Appl. Microbiol. Biotechnol. 7, 45-51 (1979).
Fiske et al, "The Colorimetric Determination of Phosphorus", The Journal of Biological Chemistry, vol. 66, No. 2, pp. 375-400 (1925).
Langer et al, "Enzymatic Regeneration of ATP", AIChE Journal, Nov. 1976, vol. 22, No. 6, pp. 1079-1090.
Maruyama et al, "ATP Production from Adenine by a Self-coupling Enzymatic Process: High-level Accumulation under Ammonium-limited Conditions", Biosci. Biotechnol. Biochem., 65(3), 644-650, 2001.
Fujio et al, Enzymatic Production of Pyrimidine Nucleotides Using *Corynebacterium ammoniagenes* Cells and Recombinant *Escherichia coli* Cells: Enzymatic Production of CDP-Choline from Orotic Acid and Choline Chloride (Part I), Biosci. Biotech. Biochem., 61(6), 956-959, 1997.
Kawai et al, "Molecular characterization of *Escherichia coli* NAD kinase", Eur. J. Biochem. 268, 4359-4365 (2001).

(Continued)

*Primary Examiner*—Sheridan Swope
(74) *Attorney, Agent, or Firm*—Nixon & Vanderhye P.C.

(57) ABSTRACT

The present invention provides a novel process for preparing nicotinamide adenine dinucleotide phosphate (NADP). The process of the present invention comprises performing phosphorylation using a polyphosphoric acid or a salt thereof and nicotinamide adenine dinucleotide (NAD$^+$) as substrates in the presence of a polyphosphate-dependent NAD$^+$ kinase from a *Mycobacterium*, wherein the reaction solution contains 0.1-15% by weight of the polyphosphoric acid or a salt thereof, and 5-150 mM of a divalent metal ion.

8 Claims, 7 Drawing Sheets

OTHER PUBLICATIONS

Kawai et al, "Molecular cloning and identification of *UTR1* of a yeast *Saccharomyces cerevisiae* as a gene encoding an NAD kinase", FEMS Microbiology Letters, vol. 200 No. 2, (2001), 181-184.

Waehneldt et al, "Phosphorylation of Nucleosides with Polyphosphoric Acid", Biochem. Biophys. Acta, 134 (1967), 1-8.

Cole et al, "Deciphering the biology of *Mycobacterium tuberculosis* from the complete genome sequence", Nature, vol. 393, Jun. 1998, 537-544.

"Enzyme Handbook", 1983, Asakura Publishing, p. 339.

Schoner et al, "Enhanced Translational Efficiency with Two-Cistron Expression System", Methods in Enzymology, vol. 185, 94-103 (1990).

Suzuki et al, "Organization of rRNA Genes in *Mycobacterium bovis* BCG", Journal of Bacteriology, Feb. 1987, vol. 169, No. 2, pp. 839-843.

Patent Abstracts of Japan, Publication No. 52-082792, published Nov. 7, 1977, Applicant Tanabe Seiyaku CO LTD, Inventor: Senhata Ichiro et al, Title: Preparation of Nicotinamide-Adenine Dinucleotide Phosphate (Abstract only).

Filippovich et al, "ATP- and Polyphosphate-dependent Bacterial NAD$^+$ Kinases", Prikladnaya Biokhimiya i Mikrobiologiya, vol. 36, No. 2 (2000), p. 117-121 (with English abstract).

Zerez et al, Arch Microbiol. May 1986;144(4):313-6 "NAD kinase from *Bacillus licheniformis*: inhibition by NADP and other properties" (Abstract only).

Kawai et al, Eur J Biochem. Aug. 2001;268(15):4359-65 "Molecular characterization of *Escherichia coli* NAD kinase."

Garavaglia, S et al J. Bacteriol. 185, 4844-4850 (2003) "Allosteric regulation of *Bacillus subtilis* NAD kinase by quinolinic acid".

Raffaelli, N et al, Biochemistry 43, 7610-7617 (2004) "Characterization of *Mycobacterium tuberculosis* NAD kinase: functional analysis of the full-length enzyme by site-directed mutagenesis" (Abstract only).

Ochiai, A et al Protein Expr. Purif. 36, 124-130 (2004) "Overexpression, purification, and characterization of ATP-NAD kinase of *Sphingomonas* sp. A1" (Abstract only).

Kawai, S et al J. Biol. Chem. 280, 39200-39207 (2005) "MJ0917 in archaeon *Methanococcus jannaschii* is a novel NADP phosphatase/NAD kinase" (Abstract only).

Lerner, F et al Biochem. Biophys. Res. Commun. 288, 69-74 (2001) "Structural and functional characterization of human NAD kinase" (Abstract only).

Stephan, C et al Int. J. Biochem. Cell Biol. 32, 855-863 (2000) "Evidence for the existence of two soluble NAD(+) kinase isoenzymes in *Euglena gracilis Z*".

Delumeau, O. et al Plant Sci. 138, 43-52 (1998) "NAD+ kinase activity, calmodulin levels during the growth of isolated cells from *Lycopersicon pimpinellifolium* and kinetic constants of the calmodulin-dependent NAD+ kinase" (as summarized from http://www.brenda-enzymes.info/literature/lit.php4?e=2.7.1.23&r=641199 retrieved Sep. 14, 2009).

Williams, M.BArch. Biochem. Biophys. 237, 80-87 (1985) "Calmodulin-dependent NAD kinase of human neutrophils" (Abstract only).

Ji, X. et al Ann. N.Y. Acad. Sci. 434, 264-266 (1984) "Immobilization of NAD kinase" (Abstract only).

Muto, S.; Z. Pflanzenphysiol. 109, 385-393 (1983) "Kinetic nature of calmodulin-dependent NAD kinase from pea seedlings" (as summarized from http://www.brenda-enzymes.info/literature/lit.php4?e=2.7.1.23&r=641200 retrieved Sep. 14, 2009).

Tseng, Y.M et al Biochim. Biophys. Acta 568, 205-214 (1979) "Isolation and characterization of yeast nicotinamide adenine dinucleotide kinase" (Abstract only).

Kawai S et al Biochem Biophys Res Commun. Sep. 16, 2000;276(1):57-63 "Inorganic Polyphosphate/ATP-NAD kinase of *Micrococcus flavus* and *Mycobacterium tuberculosis* H37Rv." (Abstract only).

Chung, A.E.; J. Biol. Chem. 242, 1182-1186 (1967) "Nicotinamide adenine dinucleotide kinase from *Azotobacter vinelandii*. I. Purification and properties of the enzyme".

Zerez et al, Arch Microbiol. May 1986;144(4):313-6 "NAD kinase from *Bacillus licheniformis*: inhibition by NADP and other properties".

Raffaelli, N et al, Biochemistry 43, 7610-7617 (2004) "Characterization of *Mycobacterium tuberculosis* NAD kinase: functional analysis of the full-length enzyme by site-directed mutagenesis".

Ochiai, A et al Protein Expr. Purif. 36, 124-130 (2004) "Overexpression, purification, and characterization of ATP-NAD kinase of *Sphingomonas* sp. A1".

Kawai, S et al J. Biol. Chem. 280, 39200-39207 (2005) "MJ0917 in archaeon *Methanococcus jannaschii* is a novel NADP phosphatase/NAD kinase".

Lerner, F et al Biochem. Biophys. Res. Commun. 288, 69-74 (2001) "Structural and functional characterization of human NAD kinase".

Delumeau, O. et al Plant Sci. 138, 43-52 (1998) "NAD+ kinase activity, calmodulin levels during the growth of isolated cells from *Lycopersicon pimpinellifolium* and kinetic constants of the calmodulin-dependent NAD+ kinase".

Williams, M.BArch. Biochem. Biophys. 237, 80-87 (1985) "Calmodulin-dependent NAD kinase of human neutrophils".

Ji, X. et al Ann. N.Y. Acad. Sci. 434, 264-266 (1984) "Immobilization of NAD kinase".

Tseng, Y.M et al Biochim. Biophys. Acta 568, 205-214 (1979) "Isolation and characterization of yeast nicotinamide adenine dinucleotide kinase".

* cited by examiner

PROCESS FOR PREPARING NICOTINAMIDE ADENINE DINUCLEOTIDE PHOSPHATE(NADP)

This application is the US national phase of international application PCT/JP02/06692 filed 2 Jul. 2002 which designated the U.S. and claims benefit of JP 201400/2001, dated 2 Jul. 2001, the entire content of which is hereby incorporated by reference.

FIELD OF THE INVENTION

The present invention relates to a process for preparing nicotinamide adenine dinucleotide phosphate (NADP).

BACKGROUND ART

NADP (nicotinamide adenine dinucleotide phosphate) has been used as a diagnostic reagent for enzymatically analyzing blood and urine [1]. Reactions for transferring phosphates to $NAD^+$ (nicotinamide adenine dinucleotide) have been previously performed by enzymatic synthesis reactions using $NAD^+$; kinases, which are often derived from microorganisms. For example, $NAD^+$ kinases from microorganisms, such as Brevibacteria and Corynebacteria as well as from yeasts and animals and plants are described in "Enzyme Handbook" 1983, Asakura Publishing, p. 339 [20]; and Matsushita H et al. 1986, Can. J. Microbiol. 32:585-590 [2].

$NAD^+$ kinases are classified into the following three main categories according to the type of phosphate donor to $NAD^+$. The relation with industrial utility is summarized in the table below.

TABLE 1

| Type | Substrate specificity of the phosphate donor | Utility for $NAD^+$ synthesis |
|---|---|---|
| 1 | ATP | x (ATP is very expensive) |
| 2 | Both polyphosphate and AT | ○ |
| 3 | Polyphosphate | ○ |

At present, industrial production of NADP relies on enzymatic processes including ATP-dependent NAD kinases (EC2.7.1.23) catalyzing phosphorylation of NAD in the presence of ATP [2]. This is partially because most of $NAD^+$ kinases are ATP-dependent $NAD^+$ kinases (type 1 in the table above) which are widely present in microorganisms, yeasts, animals and plants so that they are readily available for industrial applications. $NADP^+$ synthesis using ATP-dependent $NAD^+$ kinases must be coupled to ATP regeneration reaction because industrially expensive ATP is used. The balance between ATP regeneration reaction and $NADP^+$ synthesis reaction is summarized by the formulae below.

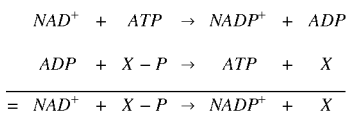

X-P: a high energy phosphate compound in living bodies, e.g. acetyl phosphate, carbamyl phosphate, phosphoenol pyruvate, ADP, etc.

X: acetic acid, carbamic acid, pyruvic acid, AMP, etc.

Enzymes used for ATP regeneration reaction: acetate kinase, carbamate kinase, pyruvate kinase, adenylate kinase, etc.

However, the above processes have such disadvantage as expensive ATP and low stability and cellular contents of the enzymes. Thus, $NAD^+$ kinases capable of utilizing inexpensively available polyphosphates as phosphate donors are desirable for industrially producing $NADP^+$ from $NAD^+$. Polyphosphates are polymers of inorganic orthophosphate residues linked via inorganic phosphate bonds energetically equivalent to the phosphate bonds of ATP (FIG. 1) [6]. Polyphosphates are commercially available in larger amounts at very lower cost as compared with ATP.

Polyphosphate-dependent NAD kinases (types 2 and 3 in Table 1) have already been reported by Murata K. et al. (Biotechnol. Bioeng., 1979 21:887-895; and Agric. Biol. Chem., 1980 44:61-68) [4], but they have not been industrially applied because of the low cellular contents thereof in the reported Brevibacterium. This may be attributed to the low activity of polyphosphate NAD kinases in cells of B. ammoniagenes.

On the other hand, Kawai et al. (Biochem, Biophys. Res. Commun., 276, pp. 57-63 (2000)) [7] describes that an open reading frame of unknown function Rv1695 from M. tuberculosis (Mycobacterium tuberculosis) of the genus Mycobacterium, H37Rv encodes a polyphosphate-dependent $NAD^+$ kinase. However, optimal reaction conditions for preparing NADP have not been examined well, and development of processes for more efficiently and inexpensively preparing NADP have been demanded.

DISCLOSURE OF THE INVENTION

An object of the present invention is to provide a novel process for preparing nicotinamide adenine dinucleotide phosphate (NADP). The process of the present invention comprises performing phosphorylation using a polyphosphoric acid or a salt thereof and nicotinamide adenine dinucleotide ($NAD^+$) as substrates in the presence of a polyphosphate-dependent $NAD^+$ kinase from a Mycobacterium, characterized in that the reaction solution contains 0.1-15% by weight of the polyphosphoric acid or a salt thereof, and 5-150 mM of a divalent metal ion.

In an embodiment of the process of the present invention, an $NAD^+$ kinase from M. tuberculosis (Mycobacterium tuberculosis) is preferably used.

In an embodiment of the process of the present invention, the reaction solution contains 2-10% by weight of a polyphosphoric acid or a salt thereof. Preferably, the reaction solution contains 50-100 mM of a divalent metal ion.

(A) shows the effect of the concentration of metaphosphoric acid on the NADP-producing activity of purified Ppnk. The NADP-producing activity was assayed in the presence of 50 (solid squares), 100 (solid circles) or 150 (solid triangles) mg/ml of metaphosphoric acid.

(B) shows the effect of the concentrations of NADP and ADP on the NADP-producing activity of purified Ppnk. The NADP-producing activity was assayed in the presence of various levels of NADP (solid circles) or ADP (open circles).

Figure 3:
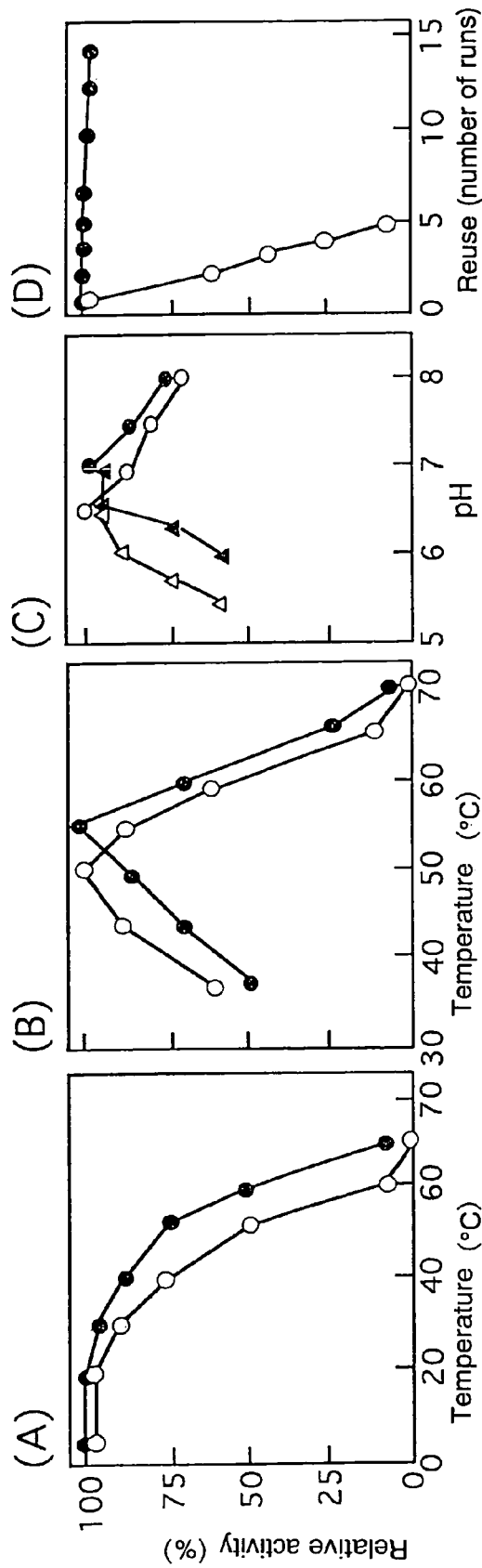

FIG. 3 shows functions of Ppnk in acetone-treated immobilized cells. The functions of Ppnk in the acetone-treated immobilized cells were evaluated by measuring the NADP-producing activity as compared with the activity in the non-immobilized acetone-treated cells. The method described in (2) Assay for NADP-producing activity in "Materials and Methods" was applied unless otherwise indicated. The maximum NADP-producing activity of Ppnk in each cell preparation was assumed to be 100%.

(A) Thermostability

The acetone-treated immobilized cells (solid circles) or the acetone-treated cells (open circles) were incubated in 0.5 ml of 5.0 mM Tris-HCl (pH 7.0) for 10 minutes at various temperatures. Persistence of the NADP-producing activity was determined.

(B) Optimal Temperature

The acetone-treated immobilized cells (solid circles) or the acetone-treated cells (open circles) were incubated at various temperatures to determine persistence of the NADP-producing activity.

(C) Optimal pH

The acetone-treated immobilized cells (solid triangles and solid circles) or the acetone-treated cells (open triangles and open circles) were incubated in 100 mM sodium acetate (solid triangles and open triangles) or Tris-HCl (solid circles and open circles) to determine persistence of the NADP-producing activity.

(D) Stability after Use

The acetone-treated immobilized cells (solid circles) or the acetone-treated cells (open circles) were repeatedly used for assaying NADP-producing activity. After each run of reaction for 1 hour, cells were washed in 5.0 mM Tris-HCl (pH 7.0) and reused for further reaction in a freshly prepared reaction mixture.

Figure 4:
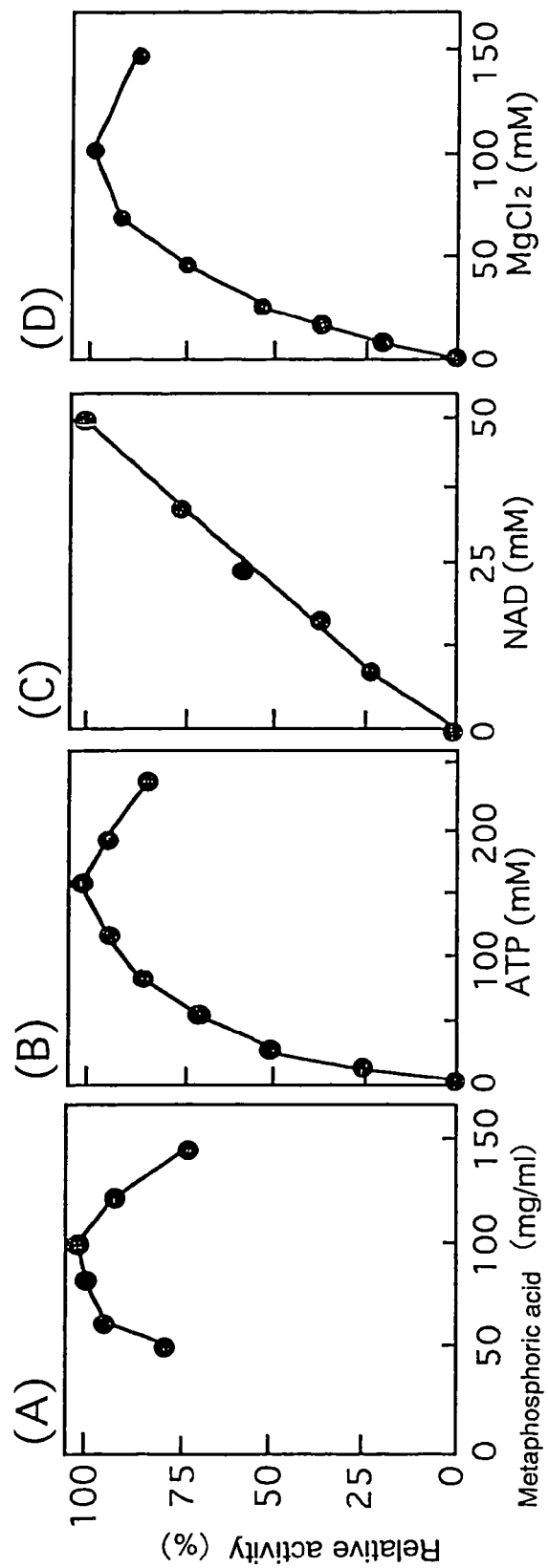

FIG. 4 shows functions of Ppnk in the acetone-treated immobilized cells. The procedure for acetone treatment and the assay for the NADP-producing activity of Ppnk in the cells were as described in 2) Assay for NADP-producing activity in "Materials and Methods" unless otherwise indicated. However, the amounts of (A) metaphosphoric acid, (B) ATP, (C) NAD and (D) Me were changed. In (A), precipitates were formed at concentrations lower than 40 mg/ml metaphosphoric acid. In (B), ATP was used in place of polyphosphate. The maximum NADP-producing activity of Ppnk was assumed to be 100%.

Figure 5:
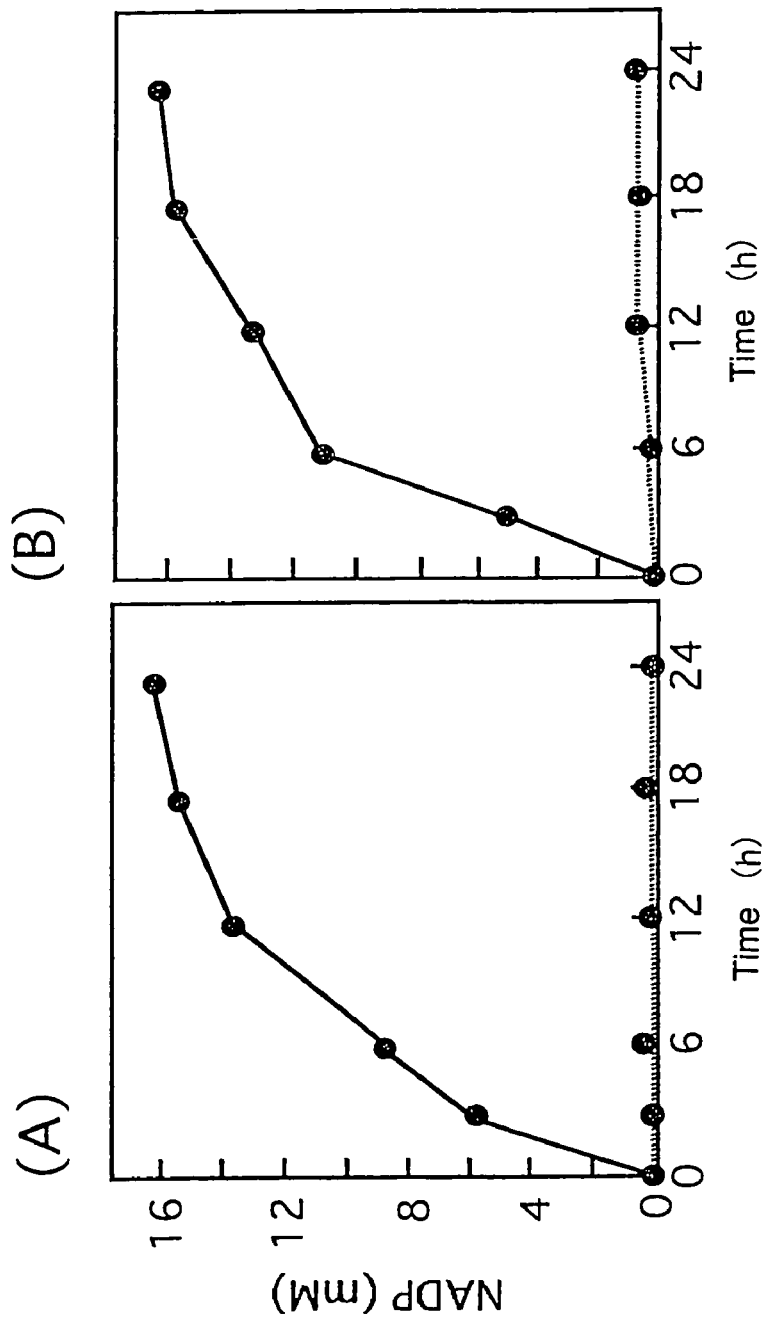

FIG. 5 shows NADP production by the acetone-treated immobilized SK27 cells (solid line) and SK45 cells (dotted line). The method described in (2) Assay for NADP-producing activity in "Materials and Methods" was applied unless otherwise indicated. A reaction for producing NADP was performed in an optimal reaction mixture (4.0 ml) consisting of 50 mM NAD, 100 mM $MgCl_2$, 100 mM Tris-HCl (pH 7.0), immobilized cells (0.10 g), and 100 mg/ml metaphosphoric acid (A) or 150 mM ATP (B). At each time indicated, 10 μl of the reaction mixture was recovered and assayed for NADP level in the mixture.

Figure 6:
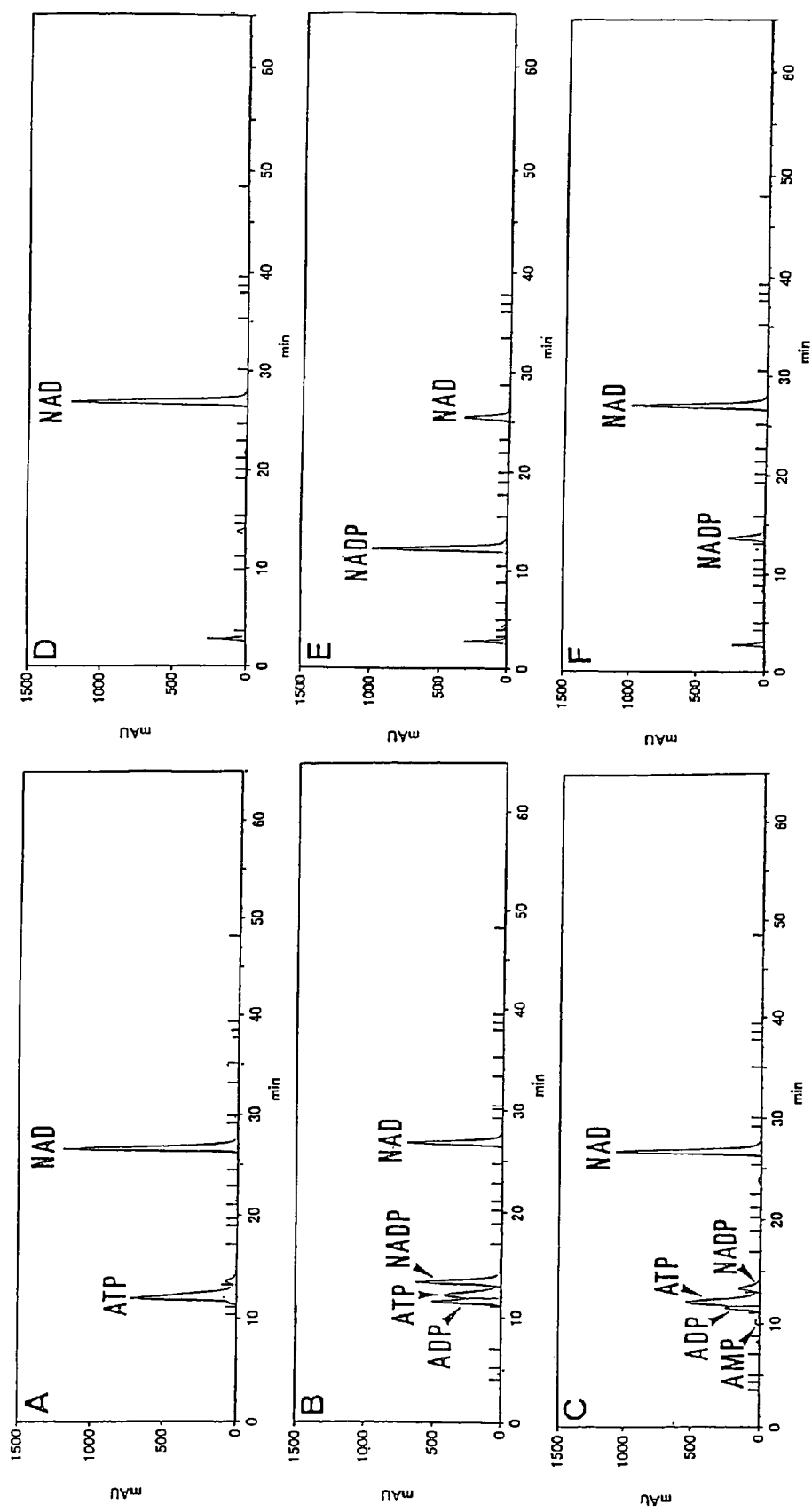

FIG. 6 shows analytic results of the reaction products. Purified Ppnk (B and E) and the immobilized cells (C and F) were used for a reaction for producing NADP in the presence of ATP (left column) or metaphosphoric acid (right column). Changes of components were tested before (A and D) and after (B, C, E, and F) the reaction.

Figure 7:
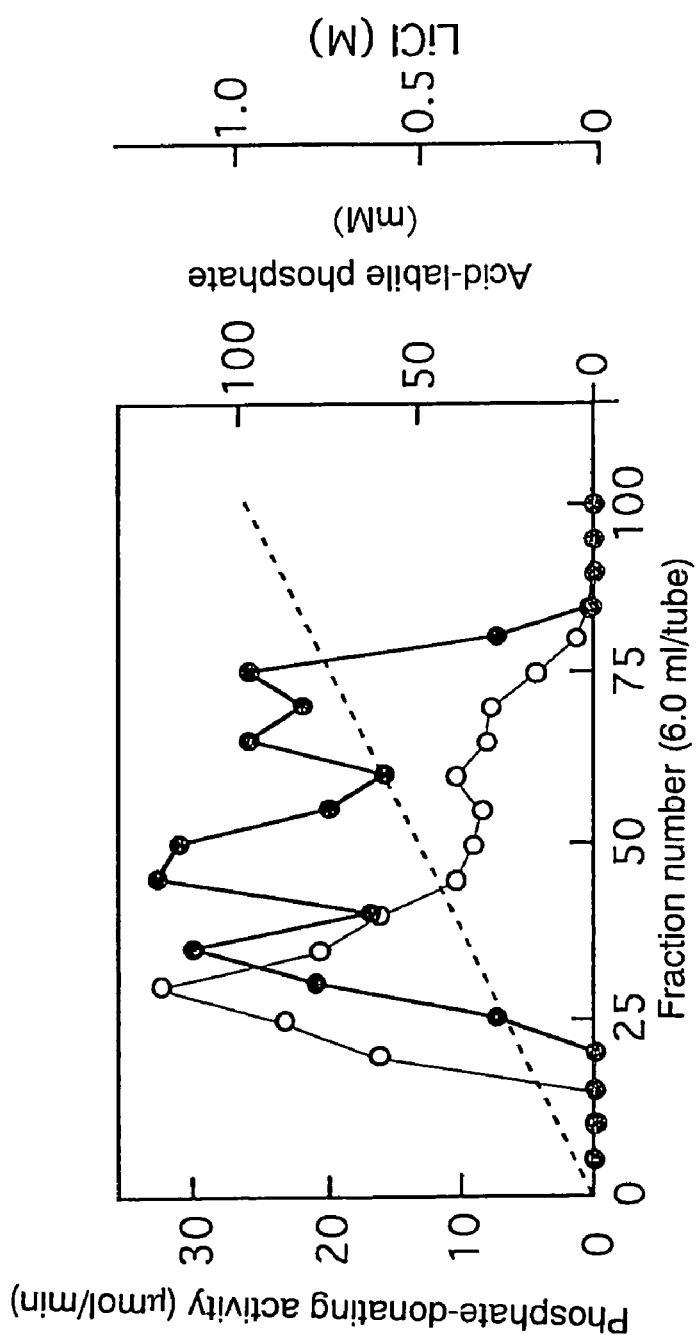

FIG. 7 shows elution patterns of phosphate donors in metaphosphoric acid on a Dowex 1×2 column. The dialysate (outer solution containing phosphate polymers) was loaded onto a Dowex 1×2 column and adsorbed phosphate polymers were eluted with a linear gradient of 0-1.0 M (pH 2.0) LiCl. Solid circles represent phosphate-donating activity, open circles represent acid-labile phosphate, and the dotted line represents the concentration of LiCl.

DETAILED DESCRIPTION OF THE INVENTION

As a result of intensive studies to solve the above problems, we found a process for efficiently and inexpensively preparing NADP to accomplish the present invention.

Therefore, the present invention provides a novel process for preparing nicotinamide adenine dinucleotide phosphate (NADP). The process of the present invention comprises performing phosphorylation using a polyphosphoric acid or a salt thereof and nicotinamide adenine dinucleotide ($NAD^+$) as substrates in the presence of a polyphosphate-dependent $NAD^+$ kinase from a *Mycobacterium*, characterized in that the reaction solution contains 0.1-15% by weight of the polyphosphoric acid or a salt thereof, and 5-150 mM of a divalent metal ion.

NAD is a coenzyme involved in oxidation-reduction (redox) reactions and its reduced form is NADH. It is also called diphosphopyridine nucleotide (DPN, DPNH), coferment, coenzyme I (CoI), etc. and it is the most abundant coenzyme found in living bodies. NAD has a structure consisting of nicotinamide mononucleotide (NMN) and adenylic acid linked via a phosphodiester bond. The oxidized form of NAD is called $NAD^+$ because the nitrogen atom in the pyridine ring exists as a pyridinium ion. $NAD^+$ is biosynthetically produced from a precursor such as tryptophan mainly in the liver in animals or glycerol and aspartate in plants through quinolinic acid. It is also synthesized from vitamins, i.e. nicotinic acid and nicotinamide. Important functions of $NAD^+$ result from the $NAD^+$ reduction coupled to the biological energy producing mechanism (oxidation reaction).

NADP was discovered as a coenzyme acting on glucose-6-phosphate dehydrogenase during studies of glucose-6-phosphate metabolism in erythrocytes. NADP basically shares the structure of NAD and contains an additional phosphate attached to the 2'-position of the ribose of adenylic acid in NAD via an ester bond. NADP abundantly occurs in the liver in living bodies but at about a half of the level of NAD. The conversion manner between the oxidized and reduced forms of NADP is similar to that of NAD, and oxidized NADP is positively charged by a pyridinium ion ($NADP^+$). NADP and NAD resemble each other in structure and reaction manner, but they are strictly distinguished by enzymes. NADP is involved in reactions catalyzed by glucose-6-phosphate dehydrogenase, isocitrate dehydrogenase, L-glutamate dehydrogenase, etc. These enzymatic reactions are widely used as indicator reactions of various coupled enzyme reactions as well as for spectroscopic quantitative assays of NADP. The assays are typically based on the difference in the absorbance $A_{340}$ of reduced NADP (NADPH). More sensitive assays can be achieved by treating $NADP^+$ with an alkali to convert into a fluorescent derivative.

Reactions for synthesizing biological components such as fatty acids and steroids involve several steps of reduction using NADPH as a major hydrogen donor. In contrast, not $NADP^+$ but $NAD^+$ and flavin protein (FP) are involved in oxidation processes as found in decomposition systems-energy production systems (glycolysis, citrate pathway, β-oxidation of fatty acids). NADP and NAD clearly exist in reciprocal redox states and have distinct functions in cells.

$NAD^+$ Kinases $NAD^+$ kinases are enzymes transferring phosphate groups of substrates to the 2'-position of the ribose of adenylic acid of $NAD^+$ to produce $NADP^+$. Conventionally, ATP has been normally used as a phosphate-donating substrate. $NAD^+$ kinases used in the processes of the present invention are characterized as polyphosphate-dependent NAD+ kinases utilizing polyphosphate or both polyphosphate and ATP as phosphate-donating substrate. In other words, the process of the present invention does not use ATP which was conventionally used as a phosphate donor. Thus, the reaction mixture solution is free from ADP or AMP, byproducts due to the conventional use of ATP during phosphate transfer reactions catalyzed by NAD+ kinases. Thus, high-purity NADP+ can be obtained in an NAD+ kinase-mediated reaction mixture solution.

Figure 1:
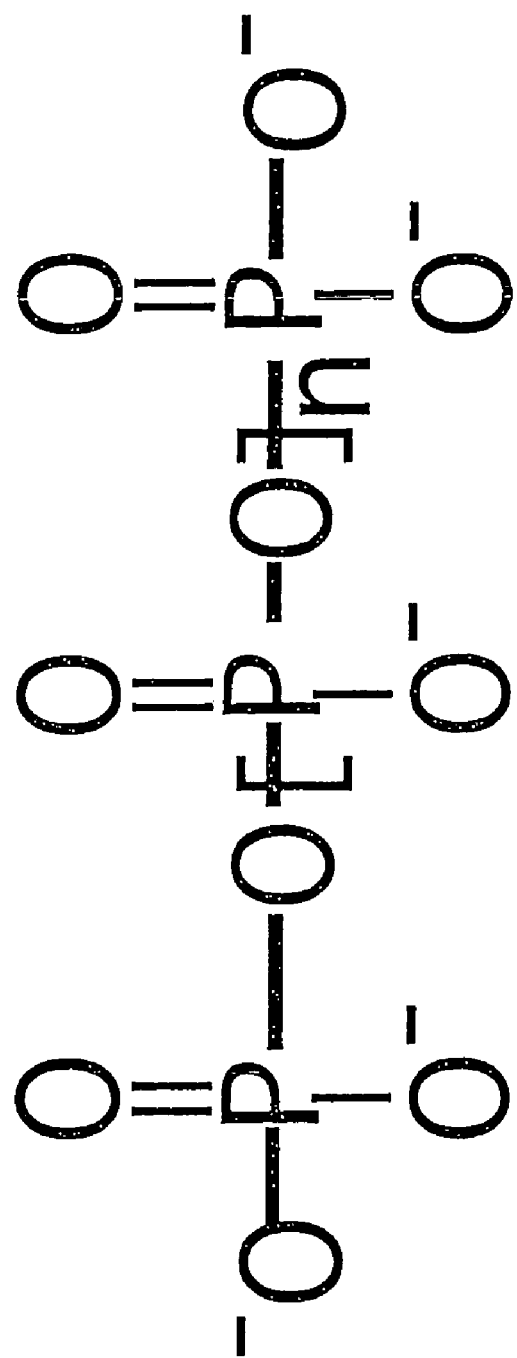
FIG. 1 shows the structure of inorganic polyphosphate [poly(P)] having a chain length of n+2.

Polyphosphates are polymers of inorganic orthophosphate residues linked via inorganic phosphate bonds energetically equivalent to the phosphate bonds of ATP as shown in FIG. 1 (FIG. 1) [6]. In FIG. 1, n represents the degree of condensation. Preferably, n is, but not limited to, 3 to 32. Relative reactivities of NAD+ kinases from *M. tuberculosis* (*Mycobacterium tuberculosis*) of the present invention and that from *Micrococcus flavus* as a control in relation to the degree of condensation of polyphosphate are described in detail by Kawai et al. (Biochem. Biophys. Res. Commun., 276, pp. 57-63 (2000)) [7]. Polyphosphates are commercially available in larger amounts at very lower cost as compared with ATP. Preferred polyphosphates used in the present invention include, but not limited to, metaphosphoric acid, hexametaphosphoric acid and salts thereof. Metaphosphoric acid and salts thereof are preferred. Polyphosphates are available from, for example, Wako Pure Chemical Industries, Sigma-Aldrich, Merck, etc.

Metaphosphoric acid is also called glacial phosphoric acid and represented by general formula $(HPO_3)_n$. Normally, it exists as a polymer such as trimer or tetramer of cyclic or linear polymetaphosphoric acids. As used herein, "metaphosphoric acid" also includes such trimer or tetramer cyclic or linear polymetaphosphoric acids. Polymetaphosphoric acid is a cyclic compound formed of phosphate groups linked by anhydride bonds and represented by general formula $H_nP_nO_{3n}$. It is a viscous liquid at room temperature, but becomes a glass-like solid solution upon cooling. Aqueous solutions are acidic and readily decomposed into orthophosphoric acid upon heating. It is hydrolyzed by metaphosphatase to open the ring into polyphosphoric acid. In the living world, high molecular polymers are found in bacteria, fungi and algae or the like, while metaphosphoric acids having low degrees of condensation such as trimetaphosphoric acid are found in yeasts and some bacteria. The phosphate anhydride linkage is the so-called high energy phosphate linkage. Reactions catalyzed by polyphosphate kinases are reversible and seem to be used for high energy phosphate linkage and phosphate storage.

Polyphosphate-Dependent NAD+ Kinases from a *Mycobacterium*

The NAD+ kinases of the present invention are derived from a *Mycobacterium* such as *M. tuberculosis* (*Mycobacterium tuberculosis*), *M. leprae*, *M. bovis*, *M. avium*, *M. paratuberculosis*, *M. smegmatis*, *M. chlorophenolicum*, *M. diernhoferi*, *M. forluitum*, *M. phlei* and *M. vaccae*. Detailed descriptions of strains belonging to the genus *Mycobacterium* can be found in e.g. Institute for Fermentation (URL:ifo.or.jp) or American Type Culture Collection (URL:atcc.org).

The NAD+ kinases of the present invention utilize polyphosphate or both polyphosphate and ATP as phosphate-donating substrate. They preferably have a reactivity to polyphosphate of 60% or more, more preferably 80% or more, still more preferably 100% or more, most preferably 120% or more as compared with the reactivity to ATP.

The NAD+ kinase proteins of the present invention are not limited to any sources or preparation processes so far as they have characteristics described herein. That is, the NAD+ kinase proteins of the present invention may be any of those natural proteins, or expressed from recombinant DNAs by genetic engineering techniques, or chemically synthesized. Alternatively, the purified proteins may be used in an immobilized state or cells expressing said proteins may be used in an immobilized state in the present invention, as described below.

The NAD+ kinases from the genus *Mycobacterium* of the present invention are preferably derived from *M. tuberculosis* (*Mycobacterium tuberculosis*). A typical NAD+ kinase herein is a protein having the amino acid sequence of SEQ ID NO:1 consisting of amino acid residues No. 1-No. 307. SEQ ID NO:1 is an amino acid sequence deduced from the nucleotide sequence of an open reading frame of unknown function Rv1695 from *M. tuberculosis* (*Mycobacterium tuberculosis*) of the genus *Mycobacterium*, H37Rv described by Kawai et al. (Biochem. Biophys. Res. Commun., 276, pp. 57-63 (2000)) [7]. The genomic fragment Rv1695 has been deposited with The Sanger Center (see URL:sanger.ac.uk/Projects/M. tuberculosis/cosmids.stml The NAD+ kinase from *Mycobacterium* or the NAD+ kinase from *M. tuberculosis* is hereinafter sometimes referred to as "Ppnk (Polyphosphate-dependent NAD kinase)".

Another currently known NAD+ kinase from *Mycobacteria* is a sequence from *M. leprae*. Specifically, BLAST searches based on the primary amino acid sequence of Ppnk protein from *M. tuberculosis* (Rv1695: *Mycobacterium tuberculosis* H37Rv) revealed homology to the known gene sequences. The results are shown below.

| Homology to the primary amino acid sequence of Ppnk | |
|---|---|
| Microorganisms | Homology |
| Mycobacterium tuberculosis | 100% |
| Mycobacterium leprae | 93% |
| Streptomyces coelicolor | 70% |

It is well known that naturally occurring proteins include variant proteins having one or more amino acid changes resulting from e.g. the presence of a genetic variations caused by different species or ecotypes producing them. As used herein, the term "amino acid change" means to include substitutions, deletions, insertions and/or additions of one or more amino acids. The protein of the present invention typically has the amino acid sequence of SEQ ID NO:1 based on the presumption from the nucleotide sequence of the gene. However, it is not limited to only the protein having this sequence, but intended to encompass any homologous proteins having characteristics defined herein. For example, proteins lacking a part of the amino acid sequence of SEQ ID NO:1 can be used for the preparation process of the present invention so far as they have the property of utilizing polyphosphate or both polyphosphate and ATP as phosphate-donating substrates. The "amino acid change" involves one or more amino acids, preferably 1-20, more preferably 1-10, most preferably 1-5 amino acids.

Thus, the NAD+ kinases from the genus *Mycobacterium* of the present invention include polypeptides having an identity of at least 70% or more to SEQ ID NO:1 and polyphosphate-dependent NAD+ kinase activity. The identity is at least 70% or more, preferably 75% or more, more preferably 80% or more, still more preferably 90% or more, most preferably 95% or more.

The percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio., 48:443 (1970)) and available from the University of Wisconsin Genetics Computer Group (UWGCG). The preferred default parameters for the GAP program include: (1) a scoring matrix, blosum62, as described by Henikoff et al. (Proc. Natl. Acad. Sci. USA, 89:10915 (1992)); (2) a gap weight of 12; (3) a gap length weight of 4; and (4) no penalty for end gaps.

Other programs used by those skilled in the art of sequence comparison may also be used. The percent identity can be determined by comparing sequence information using the BLAST program described by Altschul et al. (Nucl. Acids. Res. 25, pp. 3389-3402, 1997), for example. This program is available at the website of National Center for Biotechnology Information (NCBI) or DNA Data Bank of Japan (DDBJ) on the Internet. Various conditions (parameters) for homology searches with the BLAST program are described in detail on the site, and searches are normally performed with default values though some settings may be appropriately changed.

Generally, modified proteins containing a change from one to another amino acid having similar properties (such as a change from a hydrophobic amino acid to another hydrophobic amino acid, a change from a hydrophilic amino acid to another hydrophilic amino acid, a change from an acidic amino acid to another acidic amino acid or a change from a basic amino acid to another basic amino acid) often have similar properties to those of the original protein. Methods for preparing such recombinant proteins having a desired variation using genetic engineering techniques are well known to those skilled in the art and such variant proteins are also included in the scope of the present invention.

The present invention further includes polypeptides with or without associated native-pattern glycosylation. Polypeptides expressed in yeast or mammalian expression systems (e.g., COS-1 or COS-7 cells) may be similar to or significantly different from a native polypeptide in molecular weight and glycosylation pattern, depending upon the choice of an expression system. Expression of polypeptides of the invention in bacterial expression systems, such as E. coli, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Processes for Preparing NAD$^+$ Kinase Proteins

The Ppnk protein of the present invention may be purified from M. tuberculosis strain H37Rv, for example, according to known procedures. Cells, of M. tuberculosis H37Rv can be dissolved in an appropriate buffer (that can be selected from phosphate buffers having buffer capacity in a pH range of 6-8 such as Tris-HCl buffer and various Good's buffers) and then successively fractionated by molecular sieve (gel filtration) chromatography, Blue affinity chromatography, anion exchange chromatography and hydrophobic chromatography to give a pure sample. During purification steps, the NAD$^+$ kinase activity determined by a known method can be used as an indicator.

Alternatively, said protein can be obtained in mass by genetic engineering techniques by transducing a DNA sequence containing nucleic acid residues No. 1-No. 921 of SEQ ID NO:2 encoding Ppnk of SEQ ID NO:1 or a part thereof into E. coli, yeasts or cells of insect or certain animal cells using an expression vector capable of being amplified in each host and expressing the DNA sequence.

The amino acid sequence of the human NAD$^+$ kinase protein and the DNA sequence encoding it are disclosed herein as SEQ ID NOs:1 and 2. They can be wholly or partially used to readily isolate a gene encoding a protein having a similar physiological activity from other species using genetic engineering techniques including hybridization and nucleic acid amplification reactions such as PCR. In such cases, the proteins encoded by such genes can also be used in the present invention.

Hybridization conditions used for screening homologous genes are not specifically limited, but stringent conditions are generally preferred, such as 6×SSC, 5×Denhardt's solution, 0.1% SDS at 25-68° C. The hybridization temperature here is more preferably 45-68° C. (without formamide) or 25-50° C. (50% formamide). It is well known to those skilled in the art that DNAs containing a nucleotide sequence having a homology equal to or higher than a certain level can be cloned by appropriately selecting hybridization conditions such as formamide level, salt level and temperature, and all of thus cloned homologous genes are included in the scope of the present invention.

Nucleic acid amplification reactions here include reactions involving temperature cycles such as polymerase chain reaction (PCR) (Saiki et al., 1985, Science, 230, pp. 1350-1354), ligase chain reaction (LCR) (Wu et al., 1989, Genomics, 4, pp. 560-569; Barringer et al., 1990, Gene, 89, pp. 117-122; Barany et al., 1991, Proc. Natl. Acad. Sci. USA, 88, 189-193) and transcription-based amplification (Kwoh et al., 1989, Proc. Natl. Acad. Sci. USA, 86, pp. 1173-1177) as well as isothermal reactions such as strand displacement amplification (SDA) (Walker et al., 1992, Proc. Natl. Acad. Sci. USA, 89, pp. 392-396; Walker et al., 1992, Nuc. Acids Res., 20, pp. 1691-1696), self-sustained sequence replication (3SR) (Guatelli et. al., 1990, Proc. Natl. Acad. Sci. USA, 87, pp. 1874-1878), and Qβ replicase system (Lizardi et al., 1988, Bio-Technology, 6, pp. 1197-1202). Other reactions such as nucleic acid sequence-based amplification (NASBA) using competitive amplification of a target nucleic acid and a variant sequence disclosed in European Patent No. 0525882 can also be used. PCR is preferred.

Homologous genes cloned by hybridization or nucleic acid amplification reactions as above have an identity of at least 70% or more, preferably 80% or more, more preferably 90% or more, most preferably 95% or more to the nucleotide sequence shown as SEQ ID NO:2 in the Sequence Listing.

The percent identity may be determined by visual inspection and mathematical calculation. Alternatively, the percent identity of two nucleic acid sequences can be determined by comparing sequence information using the GAP computer program, version 6.0 described by Devereux et al. (Nucl. Acids Res., 12:387 (1984)) and available from the University of Wisconsin Genetics Computer Group (UWGCG). The preferred default parameters for the GAP program include: (1) a unitary comparison matrix (containing a value of 1 for identities and 0 for non-identities) for nucleotides, and the weighted comparison matrix of Gribskov and Burgess, Nucl. Acids Res., 14:6745 (1986), as described by Schwartz and Dayhoff, eds., Atlas of Protein Sequence and Structure, National Biomedical Research Foundation, pp. 353-358 (1979); (2) a penalty of 3.0 for each gap and an additional 0.10 penalty for each symbol in each gap; and (3) no penalty for end gaps. Other programs used by one skilled in the art of sequence comparison may also be used.

Recombinant vectors for integrating a gene to express a protein herein can be prepared by known methods. Methods for integrating a DNA fragment of the gene of the present invention into a vector such as a plasmid are described in e.g. Sambrook, J. et al, Molecular Cloning, A Laboratory Manual (2nd edition), Cold Spring Harbor Laboratory, 1.53 (1989). Commercially available ligation kits (e.g. available from Takara Bio Inc.) can be conveniently used. Thus obtained recombinant vectors (e.g. recombinant plasmids) are transferred into host cells (e.g. *E. coli* JM109, BL21(DE3)pLysS, TB1, LE392 or XL-1Blue), preferably JM109 (e.g. available from Takara Bio BL21(DE3)pLysS (Novagen, Darmstadt, Germany).

Suitable methods for introducing a plasmid into a host cell include the Hanahan method (Hanahan, D., J. Mol. Biol., 166: pp. 557-580 (1983)) or the use of calcium phosphate or calcium chloride/rubidium chloride, electroporation, electroinjection, chemical treatment with PEG or the like, the use of a gene gun described in Sambrook, J. et al., Molecular Cloning, A Laboratory Manual (2nd edition), Cold Spring Harbor Laboratory, 1.74 (1989).

Vectors can be conveniently prepared by linking a desired gene by a standard method to a recombination vector available in the art (e.g. plasmid DNA). Specific examples of suitable vectors include, but are not limited to, *E. coli*-derived plasmids such as pET3a (Novagen), pTRP (Japanese Patent Public Disclosure No. 103278/96), pBluescript, pUC18, pUC19, pBR322, preferably pET3a or pTRP. In constructing expression vectors, dicistronic systems may be used for rapid transcription to mRNAs. Detailed descriptions of dicistronic systems are found in e.g. Brigitte E. et al., Method in Enzymology 185: pp. 94-103, 1990 [21]. A combinations of the vector pTRP with a dicistronic system, i.e. the vector pTRP-2cis can also be used.

As a preferred embodiment of the present invention, a transformant pET3a-NADK/BL21(DE3)pLysS obtained by transducing an expression vector pET3a-NADK containing the ppnk gene into a host cell BL21(DE3)pLysS was deposited on Jun. 20, 2001 with the International Patent Organism Depositary (IPOD) of the National Institute of Advanced Industrial Science and Technology (residing at Tsukuba Central 6, 1-1-1 Higashi, Tsukuba-city, Ibaraki-prefecture, 305-8566, Japan) under FERM P-18383. Similarly, a transformant pTRP-2cis-NADK/JM109 obtained by transducing an expression vector pTRP-2cis-NADK containing the ppnk gene into a host cell JM109 was deposited on Jun. 20, 2001 with the International Patent Organism Depositary of the National Institute of Advanced Industrial Science and Technology (residing at Tsukuba Central 6, 1-1-1 Higashi, Tsukuba-city, Ibaraki-prefecture, 305-8566, Japan) under FERM P-18384.

Expression vectors are especially useful for the purpose of producing a desired protein. The types of expression vectors are not specifically limited so far as they can express a desired gene in various prokaryotic and/or eukaryotic host cells to produce a desired protein. Preferred known vectors include expression vectors for *E. coli* such as pQE-30, pQE-60, pMAL-C2, pMAL-p2, pSE420; expression vectors for yeasts such as pYES2 (genus *Saccharomyces*), pPIC3.5K, pPIC9K, pAO815 (all genus *Pichia*); and expression vectors for insects such as pBacPAK8/9, pBK283, pVL1392, pBlueBac4.5.

An example of an expression vector for use in mammalian host cells is a vector constructed as disclosed by Okayama and Berg (Mol. Cell. Biol. 3:280 (1983)). A useful system for stable high level expression of mammalian cDNAs in C127 murine mammary epithelial cells can be constructed substantially as described by Cosman et al. (Mol. Immunol. 23:935 (1986)). Alternatively, suitable vectors for in vivo or in vitro expression in nerve cells include adenovirus vectors or a modified vector (pEF-CITE-neo, Miyata, S et al., Clin. Exp. Metastasis, 16: pp. 613-622, 1998) of pEF-BOS vector (Mizushima, S. et al., Nucl. Acid Res. 18: p. 5322, 1990).

Transformants can be prepared by introducing a desired expression vector into a host cell. Suitable host cells are not specifically limited so far as they are compatible with the expression vector and can be transformed therewith, and include various cells such as naturally occurring cells or artificially established recombinant cells commonly used in the technical field of the present invention. Examples are bacteria (*Escherichia, Bacillus*), yeasts (Saccharomyces, Pichia), animal cells, insect cells, plant cells, etc.

Host cells are preferably *E. coli*, yeasts or insect cells, specifically *E. coli* such as M15, JM109, BL21; yeasts such as INVSc1 (the genus *Saccharomyces*), GS115, KM71 (all the genus *Pichia*); insect cells such as BmN4, silkworm larva. Examples of animal cells are those derived from mouse, *Xenopus*, rat, hamster, simian or human or culture cell lines established from these cells. Plant cells include those derived from tobacco, *Arabidopsis*, rice, maize, wheat, etc., but are not specifically limited so far as they can be cell-cultured.

When a bacterium, especially *E. coli* is used as a host cell, the expression vector generally consists of at least a promoter/operator region, a start codon, a gene encoding a desired Ppnk protein, a stop codon, a terminator and a replicable unit.

When a yeast, plant cell, animal cell or insect cell is used as a host cell, the expression vector generally preferably contains at least a promoter, a start codon, a gene encoding a desired Ppnk protein, a stop codon and a terminator. It may also contain a DNA encoding a signal peptide, an enhancer sequence, non-translated 5' and 3' regions of the desired gene, a selectable marker or a replicable unit, etc., if desired.

A preferred start codon in vectors of the present invention is a methionine codon (ATG). A stop codon may be conventional stop codons (e.g. TAG, TGA, TAA).

The replicable unit refers to a DNA capable of replicating the whole DNA sequence in a host cell, and means to include natural plasmids, artificially modified plasmids (plasmids prepared from natural plasmids) and synthetic plasmids, etc. Preferred plasmids are pQE30, pET or pCAL or their artificial modifications (DNA fragments obtained by treating pQE30, pET or pCAL with suitable restriction endonucleases) for *E. coli*; pYES2 or pPIC9K for yeasts; and pBacPAK8/9 for insect cells.

Enhancer sequences and terminator sequences may be those commonly used by those skilled in the art such as those derived from SV40.

Conventional selectable markers can be used by standard methods. Examples are genes resistant to antibiotics such as tetracycline, ampicillin, kanamycin, neomycin, hygromycin or spectinomycin.

Expression vectors can be prepared by continuously and circularly linking at least said promoter, start codon, gene encoding the desired Ppnk protein, stop codon and terminator region to a suitable replicable unit. During then, a suitable DNA fragment (such as a linker or a restriction site) can be applied by standard methods such as digestion with a restriction endonuclease or ligation with T4DNA ligase, if desired.

The expression vectors can be transduced into host cells by using known techniques. For example, bacteria (such as *E. coli, Bacillus subtilis*) can be transformed by the method of Cohen et al. [Proc. Natl. Acad. Sci. USA, 69, 2110 (1972)], the protoplast method [Mol. Gen. Genet., 168, 111 (1979)] or the competent method [J. Mol. Biol., 56, 209 (1971)]; *Saccharomyces cerevisiae* can be transformed by the method of Hinnen et al. [Proc. Natl. Acad. Sci. USA, 75, 1927 (1978)] or the lithium method [J.B. Bacteriol., 153, 163 (1983)]; plant cells can be transformed by the leaf disc method [Science, 227, 129 (1985)] or electroporation [Nature, 319, 791 (1986)]; animal cells can be transformed by the method of Graham [Virology, 52, 456 (1973)]; and insect cells can be transformed by the method of Summers et al. [Mol. Cell. Biol., 3, 2156-2165 (1983)].

Purification and isolation of the Ppnk protein of the present invention can be accomplished by appropriately combining conventional methods for purifying and isolating proteins, such as ammonium sulfate precipitation, ion exchange chromatography (e.g. DEAE-Cellulofine, MonoQ, Q Sepharose).

When the $NAD^+$ kinase protein of the present invention accumulates in host cells, for example, the host cells are collected by centrifugation or filtration or the like and suspended in a suitable buffer (e.g. a buffer such as Tris buffer, phosphate buffer, HEPES buffer or MES buffer at a concentration of about 10 mM-100 mM and desirably in a pH range of 5.0-8.0 though the pH depends on the buffer used), then the cells are disrupted by a method suitable for the host cells used (e.g. ultrasonication) and centrifuged to collect the contents of the host cells. When the $NAD^+$ kinase protein of the present invention is secreted outside host cells, however, the host cells and the culture medium are separated by centrifugation or filtration or the like to give a culture filtrate. The host cell lysate or the culture filtrate can be used to isolate/purify the protein directly or after ammonium sulfate precipitation and dialysis. The isolation/purification can be performed as follows. When the protein of interest is tagged with 6×histidine, GST, maltose-binding protein or the like, conventional methods based on affinity chromatography suitable for each tag can be used. When the protein of the present invention is produced without using these tags, the method based on antibody affinity chromatography can be used, for example. These methods may be combined with ion exchange chromatography, gel filtration or hydrophobic chromatography, isoelectric chromatography or the like.

Examination on Reaction Conditions for Preparing NADP

Processes for preparing NADP according to the present invention rely on a reaction using polyphosphate and $NAD^+$ as substrates in the presence of a polyphosphate-dependent $NAD^+$ kinase.

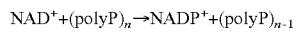

$$NAD^+ + (polyP)_n \rightarrow NADP^+ + (polyP)_{n-1}$$

The efficiency of the above reaction is influenced by various conditions such as temperature, pH, the type of polyphosphate, the concentration of polyphosphate in the reaction solution, and the level and type of metal ions. After examining various conditions, we found that the efficiency of the reaction is especially influenced by the concentrations of polyphosphate and metal ions in the reaction solution.

The concentration of polyphosphoric acid or a salt thereof in the reaction solution is 0.1-15% by weight, preferably 2-10% by weight, more preferably 5-10% by weight, most preferably about 10% by weight of the reaction solution. The type of polyphosphate is not specifically limited. For example, it can be appropriately selected from metaphosphoric acid, hexametaphosphoric acid and the like described above.

The above reaction catalyzed by a polyphosphate-dependent $NAD^+$ kinase requires the presence of a metal ion, especially a divalent metal ion. The concentration of the divalent metal ion in the reaction solution is 5-150 mM, preferably 50-150 mM, more preferably 50-100 mM, most preferably 100 mM. The divalent metal ion is not specifically limited, but preferably selected from magnesium ion or manganese ion. Especially preferred is magnesium ion. The metal ion is preferably contained in the reaction solution as a chloride, sulfate or nitrate.

In order to obtain $NADP^+$ at a high yield after the completion of the $NAD^+$ kinase-mediated reaction, it is important not only to attain a high phosphate transfer efficient from $NAD^+$ but also to stably maintain $NADP^+$ once synthesized. $NADP^+$ is known to be less stable to heat and pH than $NAD^+$ (e.g. see Year 2000 Catalog of Oriental Yeast, Co., Ltd.). Thus, conditions for the $NAD^+$ kinase-mediated reaction should be selected in such a manner that $NADP^+$ has a stable composition.

The reaction should preferably be performed under the conditions of, but not limited to, a temperature of 20-37° C., more preferably 37° C. The pH is preferably 5-8, more preferably 6-7. Processes of the present invention use an $NAD^+$ kinase from *Mycobacteria* having an optimal working pH range in which $NADP^+$ is more stable (in a range of pH 3-7).

Forms of $NAD^+$ Kinases

The $NAD^+$ kinases used in the processes of the present invention may be in the form of a solubilized protein purified from natural sources or recombinant host cells, or an immobilized enzyme obtained by immobilizing the solubilized protein. Alternatively, cells expressing an kinase protein may be directly immobilized by a chemical treatment such as acrylamide and used as immobilized enzymatic cells.

Methods for purifying $NAD^+$ kinase proteins from natural sources or recombinant host cells were described in detail above in the section of "Processes for preparing $NAD^+$ kinase proteins". The resulting purified protein can be used as a solubilized protein. Alternatively, the purified protein can be immobilized and used as an immobilized enzyme. Enzymes can be immobilized by known methods. For example, a purified $NAD^+$ kinase protein can be immixed with an activated gel (e.g. Formyl-Cellulofine gel (from Chisso Co.)) under non-deactivating mild conditions to immobilize the purified $NAD^+$ kinase protein on the insolubilized gel. Detailed descriptions of procedures for immobilizing purified proteins are found in e.g. catalogs of SEIKAGAKU CORPORATION Co. for the use of Formyl-cellulofine gel. Activated gels are also described in many other documents such as the manufacturer's manual of Pharmacia Biotech.

Alternatively, it is more effective to immobilize microbial cells expressing an $NAD^+$ kinase protein or to use a cellular subfraction to adopt a method based on a metabolic pathway present in the microbial cells such as a glycolytic system. Typical examples are described in Murayama A et al. Biosci. Biotech. Biochem. 2001 65:644-650 [14] and Fujio T et al. Biosci. Biotech. Biochem. 1997 61:956-959 [15].

Known methods for immobilizing microbial cells use carrageenan or acrylamide gel. Methods for immobilizing microbial cells are described in e.g. Murata K et al. Biotechnol. Bioeng., 1979 21:887-895, supra. [4]. Various improvements were added e.g. by disrupting cellular membranes by a treatment with an organic solvent such as acetone to facilitate the action of intracellular soluble enzyme after microbial cells have been immobilized.

In Example 4 below as a non-limiting example, host cells overexpressing Ppnk protein were immobilized in a polyacrylamide gel matrix and treated with acetone to increase the permeability of the substrates [NAD and polyphosphate (poly$(P)_n$)] and/or products [NAD and polyphosphate $(poly(P)_{n-1})$].

Specifically, harvested host cells were first washed with cooled saline and then immobilized by the method described in [10] with some modifications. Host cells are first suspended in 0.75M Tris-HCl (pH 8.8) and thoroughly mixed with an acrylamide solution, then left in ice water at 0-4° C. for 10 minutes to 1 hour. The acrylamide solution comprises e.g. 10-50% acrylamide, 0.2-1% N,N'-methylenebisacrylamide, 0.1-0.5% N,N,N',N'-tetramethylethylenediamine, and 0.1-0.5% potassium ammonium persulfate. The resulting gel is cut into cubes (e.g., 3.0 mm×3.00 mm×3.0 mm).

The above gel may be further treated with acetone. Specifically, the cubic gel is suspended in acetone and incubated with mild stirring at 0° C. for 2 minutes to 20 minutes. The gel is thoroughly washed with cooled 5.0 mM Tris-HCl buffer (pH 7.0) and stored in a similar buffer containing e.g. 0.01 mM to 1 mM $NAD^+$ and 0.01 mM to 10 mM $MgCl_2$ at about 4° C. before use.

In Example 4, 5.0 g (wet weight) of SK27 cells or SK45 cells were immobilized in 15 ml of polyacrylamide gel, i.e. in a ratio of about 0.33 g (wet weight) of cells/ml gel.

NADP production by using purified Ppnk protein has several disadvantages. For example, (i) lengthy and complex operations are required for purifying Ppnk protein, (ii) Ppnk is not very stable, and (iii) the enzyme cannot be reused unless it is insolubilized. In contrast, immobilized cells can be conveniently used because no purification of the enzyme is required and they can be applied to substrate solutions having higher ion strength. The immobilized cells have also the advantage that the enzyme can be reused because it can be readily separated from the reaction solution by filtration or other means after the completion of the reaction.

However, the immobilized cells have the following disadvantages: the amount of $NAD^+$ kinase present per unit cells is insufficient and the enzyme tends to be partially deactivated by chemical treatment during preparation of the immobilized cells. This invites problems such as the low production yield of $NADP^+$ even after a continuous enzymatic reaction for a long period (e.g. 2-7 days), generation of decomposition products by the extended reaction and coloration of the mixed solution after the completion of the reaction. These disadvantages do not occur when purified $NAD^+$ kinase proteins are used.

The present invention enabled NADP production on a commercial scale by adopting appropriate reaction conditions whichever the purified proteins, the immobilized enzymes or immobilized cells is used.

REFERENCES

1. Beutler, H. O. and Supp, M.: Coenzymes, metabolites, and other biochemical reagents, pp. 328-393. In Bergmeyer, H. U. (ed.), Methods of enzymatic analysis. Vol, 1. Verlag Chemie, Weinheim (1983).
2. Matsushita, H., Yokoyama, S., and Obayashi, A.: NADP production using thermostable NAD kinase of Corynebacterium flaccumfaciens AHU-1622. Can. J. Microbiol., 32, pp. 585-590 (1986).
3. McGuinnes, E. T. and Bulter, J. R.: NAD kinase—A review. Int. J. Biochem., 17, pp. 1-11 (1985).
4. Murata, K., Kato, J., and Chibata, I.: Continuous production of NADP by immobilized Brevibacterium ammoniagenes cells. Biotechnol. Bioeng., 21, pp. 887-895 (1979).
5. Murata, K., Uchida, T., Tani, K., Kato, J., and Chibata, I.: Metaphosphate: A new phosphoryl donor for NAD phosphorylation. Agric. Biol. Chem., 44, pp. 61-68 (1980).
6. Wood, H. G. and Clark, J. E.: Biological aspects of inorganic polyphosphates. Ann. Rev. Biochem., 57, pp. 235-260 (1988).
7. Kawai, S., Mori, S., Mukai, T., Suzuki, S., Hashimoto, W., Yamada, T., and Murata, K.: Inorganic polyphosphate/ATP-NAD kinase of Micrococcus flavus and Mycobacterium tuberculosis H37Rv. Biochem. Biophys. Res. Commun., 276, pp. 57-63 (2000).
8. Ausubel, F. M., Brent, R., Kingston, R. E., Moore, D. D., Seidman, J. G., Smith, J. A., and Struhl, K.: Current Protocols in Molecular Biology. John Wiley & Sons, Inc., New York (1994).
9. Bradford, M.: A rapid and sensitive method for the quantitation of microgram quantities of protein utilizing the principle of protein dye-binding. Anal. Biochem., 72, pp. 248-254 (1976).
10. Chibata, I., Tosa, T., and Sato, T.: Immobilized aspartase-containing microbial cells: preparation and enzymatic properties. Appl. Microbiol., 27, pp. 878-885 (1974).
11. Murata, K., Uchida, T., Tani, K., Kato, J., and Chibata, I.: Continuous production of glucose-6-phosphate by immobilized Achromobacter butyri cells. Eur. J. Appl. Microbiol. Biotechnol., 7, pp. 45-50 (1979).
12. Fiske, C. H. and Subbarow, Y.: The colorimetric determination of phosphorus. J. Biol. Chem., 66, pp. 375-400 (1925).
13. Langer, R. S., Hamilton, B. K., Gardner, C. R., Archer, M. C., and Colton, C. K.: Enzymatic regeneration of ATP. AIChE J., 22, pp. 1079-1090 (1976).
14. Maruyama, A. and Fujio, T.: ATP-production from adenine by a self-coupling enzymatic process: high-level accumulation under ammonium-limited conditions. Biosci. Biotech. Biochem., 65, pp. 644-650 (2001).
15. Fujio, T. and Maruyama, A.: Enzymatic production of pyrimidine nucleotides using Corynebacterium ammoniagenes cells and recombinant Escherichia coli cells: Enzymatic production of CDP-choline from orotic acid and choline chloride (Part I). Biosci. Biotech. Biochem., 61, pp. 956-959 (1997).
16. Kawai, S., Mori, S., Mukai, T., Hashimoto, W., and Murata, K.: Molecular characterization of Escherichia coli NAD kinase. Eur. J. Biochem., in press (2001).
17. Kawai, S., Suzuki, S., Mori, S., and Murata, K.: Molecular cloning and identification of UTR1 of a yeast Saccharomyces cerevisiae as a gene encoding an NAD kinase. FEMS Microbiol. Lett., in press (2001).
18. Waehneldt, T. V. and Fox, S.: Phosphorylation of nucleosides with polyphosphoric acid. Biochim. Biophys. Acta, 134, pp. 9-16 (1967).
19. S. T. Cole, et al.,: Deciphering the biology of Mycobacterium tuberculosis from the complete genome sequence. Nature 393, pp. 537-544 (1998).
20. "Enzyme Handbook" 1983, Asakura Publishing, p. 339.
21. Brigitte E. et al., Method in Enzymology 185: pp. 94-103 (1990).
22. Suzuki Y. et al., J. Bacteriol., 169, pp. 839-843 (1987).

EXAMPLES

The following examples further illustrate the present invention without, however, limiting the technical scope of the invention thereto. Various changes and modifications can be added to the invention by those skilled in the art on the basis of the description herein, and such changes and modifications are also included in the technical scope of the invention. Unless otherwise indicated, the following methods were used in the examples herein.

(1) Assay for the Polyphosphate-Dependent NAD Kinase Activity of Ppnk

The polyphosphate-dependent NAD kinase activity of Ppnk was assayed in a reaction mixture (1.0 ml) containing 5.0 mM NAD, 5.0 mM $MgCl_2$, 100 mM Tris-HCl (pH 7.0), 1.0 mg/ml polyphosphate and Ppnk protein as previously described [5], [7]. The polyphosphate used was metaphosphoric acid (Wako Pure Chemical Industries, Osaka, Japan). One unit of Ppnk activity was defined as the activity of producing 1.0 μmol of NADP at 37° C. in 1 hour. The specific activity was expressed in units/mg protein. The protein level was determined by using the bovine serum albumin as a standard according to the method of Bradford et al. [9].

(2) Assay for NADP-Producing Activity

A reaction for producing NADP was performed in a reaction mixture solution (4.0 ml) at 37° C. with shaking. The reaction mixture solution consists of 50 mM NAD, 100 mM $MgCl_2$, 100 mM Tris-HCl (pH 7.0), 50 mg/ml polyphosphate (metaphosphoric acid), and one of purified Ppnk (14.4 units, i.e. 0.16 mg protein) or various cell preparations [cells (0.03 g) or the immobilized cells (0.10 g) or homogenates thereof]. After the reaction for 1 hour, 10 μl of the reaction mixture was collected and enzymatically assayed for NADP using isocitrate dehydrogenase (Sigma-Aldrich Japan, Tokyo, Japan) [7]. The activity was expressed in μmol/g cells/hour.

(3) Preparation of Homogenates

Homogenates of intact cells and acetone-treated cells were prepared by disrupting cells with a sonifier (Branson, Danbury, Conn.) at 0° C. for 10 min in 5.0 ml of 5.0 mM Tris-HCl (pH 7.0). Homogenates of immobilized cells and acetone-treated immobilized cells were prepared by grinding 3.0 ml of gel with a pestle at 0° C. for 20 min in 5.0 ml of 5.0 mM Tris-HCl (pH 7.0).

Example 1

Expression of a Recombinant Ppnk Protein

1) Construction of an Expression Vector

According to the method of Kawai et al. [7], an open reading frame of unknown function Rv1695 was amplified by PCR from *M. tuberculosis* H37Rv chromosomal DNA. Specifically, chromosomal DNA of *M. tuberculosis* H37Rv was first prepared from cultured cells as described in Suzuki Y. et al., J. Bacteriol., 169, pp. 839-843 (1987) [22]. The genomic sequence of H37Rv chromosomal DNA can be found at URL: sanger.ac.uk/Projects/*M. tuberculosis*/cosmids.stml. Then, an NdeI primer having an NdeI restriction site and a BamHI antisense primer having a BamHI restriction site as shown below were used to specifically amplify Rv1695 and to permit the insertion of amplified Rv1695 into a plasmid using NdeI/BamHI sites.

NdeI primer:

```
NdeI primer:

5'-ccc ata tga ccg ctc atc gca gtg ttc tg-3'
(SEQ ID NO: 3)
BamHI antisense primer:

5'-cgg atc cct act ttc cgc gcc aac cgg tc-3'
(SEQ ID NO: 4)
```

The PCR reaction solution had the following composition (in 100 μL): 1×KOD buffer (Toyobo Co., Ltd.) containing 2.5 U KOD polymerase (Toyobo Co., Ltd.), 0.25 μg *M. tuberculosis* H37Rv chromosomal DNA, 40 μmol NdeI primer, 40 μmol BamHI antisense primer, 20 nmol dNTPs and 100 nmol $MgCl_2$. The PCR reaction consisted of 25 cycles of 98° C. for 15 seconds (denaturation), 67° C. for 2 seconds (annealing) and 74° C. for 30 seconds (extension) to give an intended PCR product of 0.93 kb.

The nucleotide sequence of the PCR product was determined and verified to be identical to Rv1965 of *M. tuberculosis* H37Rv (see URL:sanger.ac.uk/Projects/*M. tuberculosis*/cosmids.stml [19]. Then, the resulting NdeI/BamHI fragment of the ppnk gene encoding Ppnk was inserted into the *E. coli* expression plasmid pET3a (Novagen) under the control of the T7 promoter using NdeI/BamHI sites to construct an expression plasmid vector.

The nucleotide sequence of the PCR product was determined and verified to be identical to Rv1965 of *M. tuberculosis* H37Rv (see URL:sanger.ac.uk/Projects/*M. tuberculosis*/cosmids.stml [19]. Then, the resulting NdeI/BamHI fragment of the ppnk gene encoding Ppnk was inserted into the *E. coli* expression plasmid pET3a (Novagen) under the control of the T7 promoter using NdeI/BamHI sites to construct an expression plasmid vector.

2) Expression of Recombinant Proteins

The above expression vector was used to transform host cells, thereby expressing a recombinant *M. tuberculosis* Ppnk protein. The host cell strain used was *E. coli* BL21(DE3) pLysS (Novagen, Darmstadt, Germany) [7]. The expression vector pET3a-NADK containing the Ppnk gene was transformed into *E. coli* BL21(DE3)pLysS competent cells (Novagen) according to a known method to give a recombinant designated SK27. The recombinant SK27, i.e. pET3a-NADK/BL21(DE3)pLysS was deposited on Jun. 20, 2001 with the International Patent Organism Depositary of the National Institute of Advanced Industrial Science and Technology (residing at Tsukuba Central 6, 1-1-1 Higashi, Tsukuba-city, Ibaraki-prefecture, 305-8566, Japan) under the accession number FERM P-18383. As a control, the empty vector pET3a not containing the Ppnk gene was transformed into BL21 in the same manner to give a recombinant designated SK45.

Similarly, the Rv1695 gene amplified by PCR was inserted into the plasmid pTRP-2cis according to the method described in Japanese Patent Public Disclosure No. 103278/96 and Japanese Patent Public Disclosure No. 191984/98 and then transformed into the *E. coli* JM109 competent cells (Takara Bio Inc.) to give a recombinant designated pTRP-2cis-NADK/JM109. The transformant was deposited on Jun. 20, 2001 with the International Patent Organism Depositary of the National Institute of Advanced Industrial Science and Technology under the accession number FERM P-18384.

Cell cultures of SK27 (and SK45) were incubated with shaking in LB liquid medium containing 100 μg/mL ampicillin and 34 μg/mL chloramphenicol [8] at 37° C. until OD600 reached around 0.7, at which 0.4 mM isopropyl-β-D galactopyranoside (IPTG) was added and then the cultures were cooled to 18° C. Then, incubation with shaking was continued for 3 days to induce the expression of the recombinant Ppnk protein [7]. In the case of pTRP-2c-Rv1695/JM109, cultures were incubated with shaking overnight in LB liquid medium containing 100 μg/mL ampicillin at 37° C. to induce the expression of the recombinant Ppnk protein.

Example 2

NAD+ Kinase Activity of Ppnk Protein

After the transformed *E. coli* cells of Example 1 were disrupted, polyphosphate-dependent NAD+ kinase activity was recovered as soluble fraction into the lysate. The activity was tested as described in (1) Assay for the polyphosphate-dependent NAD kinase activity of Ppnk in "Materials and Methods" to show an activity level of about 6,000 units/L culture medium, i.e. 31 units/mg cells extracts. This is about 400 times higher than the activity of the NAD kinase of *Brevibacterium* ammoniagenes (0.075 units/mg) that has been conventionally used for producing NADP from NAD and polyphosphate (metaphosphoric acid) [4]. The NAD+ kinase activity of the recombinant Ppnk protein was assayed by the method of Kawai S et al. supra. [7] and one unit was defined as the activity of producing 1 μmol NADP+ at 37° C. in 60 minutes.

Example 3

Purification of the Recombinant Ppnk Protein

To purify the recombinant Ppnk protein, the frozen cell cultures of Example 1 were first thawed and resuspended at 10% (w/v) in an extraction buffer (containing 10 mM potassium phosphate buffer (pH 7.5), 0.1 mM NAD % 1 mM 2-mercaptoethanol and 0.5 mM EDTA). Then, the suspension was sonicated in ice water for 5 minutes. After centrifugation, the extract supernatant was collected.

The extract was loaded onto a column which has been packed with DEAE-Cellulofine (SEIKAGAKU CORPORATION) and has been equilibrated with the extraction buffer, and the column was thoroughly washed. As a result, NAD+ kinase activity could be recovered as a single elution peak near 0.2M NaCl by gradient elution of 0-0.5M NaCl. At this stage, the recombinant Ppnk protein including substantially no phosphatase could be obtained. The activity was tested as described in (1) Assay for the polyphosphate-dependent NAD kinase activity of Ppnk in "Materials and Methods" to show a specific activity of about 150 units/mg protein.

Enzymatic properties of the resulting purified *M. tuberculosis* Ppnk protein were evaluated and compared with the properties of a previously known polyphosphate-dependent NAD kinase from *Micrococcus* flavus. The results are shown in Table 2 below.

TABLE 2

(Enzymatic properties of Ppnk proteins)

| | *Micrococcus flavus* (control) | *M. tuberculosis* H37Rv (present invention) |
|---|---|---|
| Molecular weight (gel filtration) | 68,000 | 140,000 |
| Optimal temperature | 55° C. | 50° C. |
| Optimal pH | pH 7.0 | pH 5.5-6.5 |
| ATP/polyphosphate reaction ratio | | |
| ATP | (100%) | (100%) |
| Poly(p)$_4$ | (18%) | (121%) |
| Polyphosphate specificity | | |
| Poly(p)$_4$ | (100%) | (100%) |
| polyphosphate | (91%) | (92%) |
| metaphosphate | (58%) | (109%) |
| hexametaphosphate | (58%) | (72%) |

TABLE 2-continued (Enzymatic properties of Ppnk proteins)

| | *Micrococcus flavus* (control) | *M. tuberculosis* H37Rv (present invention) |
|---|---|---|
| Activation by metal ions (each 1 mM) | | |
| MgCl$_2$ | (100%) | (100%) |
| MnCl$_2$ | (143%) | (268%) |
| CaCl$_2$ | (65%) | (34%) |
| CoCl$_2$ | (51%) | (55%) |
| CuCl$_2$ | (33%) | (8%) |
| ZnCl$_2$ | (30%) | (30%) |
| AlCl$_3$ | (0%) | (0%) |

Comparison of enzymatic properties showed that the recombinant Ppnk protein from *M. tuberculosis* H37Rv is a preferable transferase for synthesizing NADP+ from NAD+ using polyphosphate as a phosphate donor.

Example 4

Immobilization of Cells into a Polyacrylamide Gel

NADP production by using purified Ppnk protein has several disadvantages:

(i) lengthy and complex operations are required for purifying Ppnk, (ii) Ppnk is not very stable, and (iii) the enzyme cannot be reused (unless it is insolubilized).

Ppnk protein was immobilized on an ion exchanger and used for continuous production of NADP from NAD and metaphosphoric acid. Immobilized enzyme (Ppnk) systems are currently available on a commercial scale. However, it is thought that immobilized cells can be more conveniently used than the immobilized enzyme because no purification of the enzyme is required and substrate solutions having higher ion strength can be applied. Thus, SK27 cells overexpressing Ppnk protein were entrapped in a polyacrylamide gel matrix and treated with acetone to increase the permeability of the substrates [NAD and polyphosphate (poly(P)$_n$)] and/or products [NADP and polyphosphate (poly(P)$_{n-1}$)].

Specifically, SK27 or SK45 cells cultured in Example 1 were first harvested and washed twice with 0.85% cooled saline. The cells were immobilized according to the method described in [10] with some modifications.

Specifically, 5.0 g (wet weight) of SK27 or SK45 cells were suspended in 6.0 ml of 0.75M Tris-HCl (pH 8.8). The cell suspension was thoroughly mixed with 4.5 ml of an acrylamide solution (30% acrylamide, 0.6% N,N'-methylenebisacrylamide, 0.25% N,N,N',N'-tetramethylethylenediamine, and 0.25% potassium ammonium persulfate), and then, left at 0° C. for 30 minutes. The resulting gel (15 ml) was cut into cubes (3.0 mm×3.00 mm×3.0 mm).

This was further suspended in 50 ml of acetone and incubated at 0° C. for 5 minutes with mild stirring. The gel was washed twice with cooled 5.0 mM Tris-HCl buffer (pH 7.0) and stored in 5.0 mM Tris-HCl buffer (pH 7.0) containing 0.10 mM NAD and 0.10 mM MgCl$_2$ at 4° C. before use.

By this method, 5.0 g (wet weight) of SK27 or SK45 cells were immobilized in 15 ml of polyacrylamide gel, i.e. in a ratio of about 0.33 g (wet weight) of cells/ml gel.

Example 5

NADP Production by Purified Ppnk Protein

Figure 2:
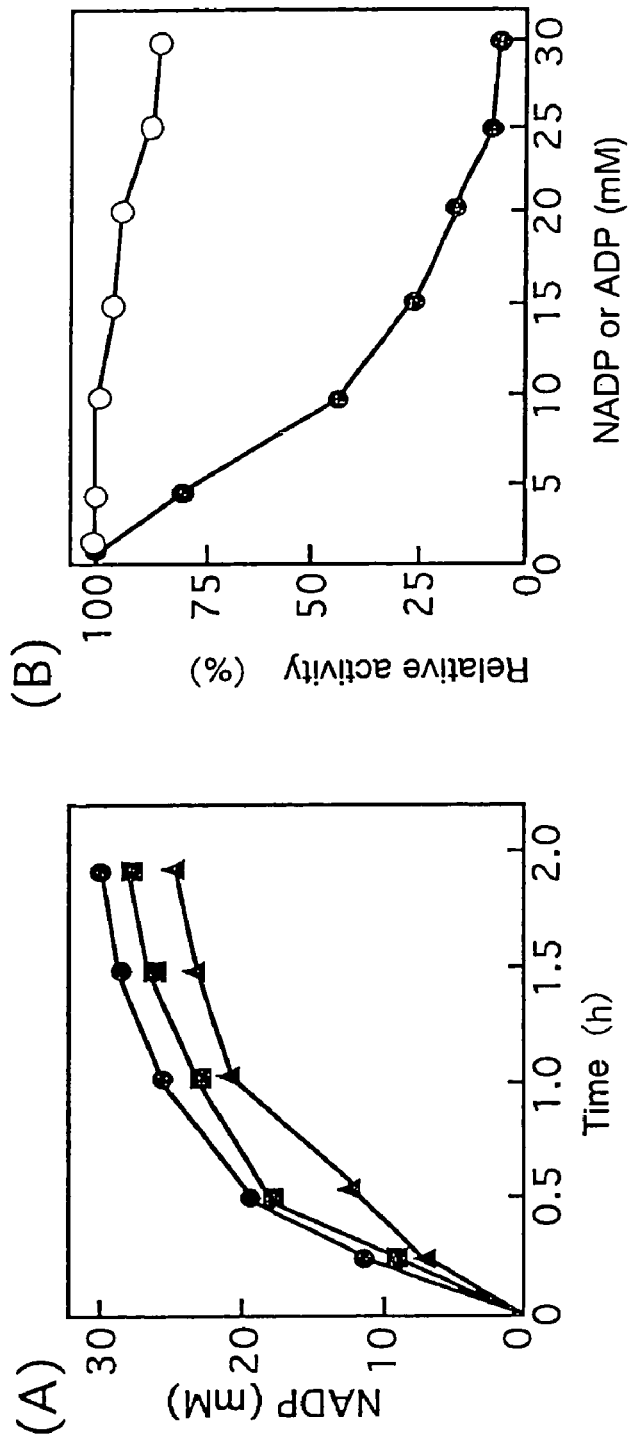
FIG. 2 shows the NADP-producing activity of the purified Ppnk protein. The method described in (2) Assay for NADP-producing activity in "Materials and Methods" below was applied unless otherwise indicated.

Ppnk (150 units/mg) purified from cell extracts of SK27 [7] was used to produce NADP. The NADP-producing activity was assayed using 14.4 units of purified Ppnk in the presence of 50 (solid squares), 100 (solid circles) or 150 (solid triangles) mg/ml of metaphosphoric acid according to the method described in (2) Assay for NADP-producing activity in "Materials and Methods". The results showed that 30 mM (27 g/l) NADP was produced from 50 mM NAD and 100 mg/ml metaphosphoric acid (FIG. 2A). However, the transfer from NAD to NADP remained less than 60% irrespective of the concentration of metaphosphoric acid (FIG. 2A).

The low transfer efficiency is attributed to the fact that the polyphosphate-dependent NAD kinase activity of Ppnk protein was inhibited by the NADP produced. In fact, the polyphosphate-dependent NAD kinase activity of Ppnk is significantly inhibited by NADP but not inhibited by ADP. The inhibition is substantially completely induced by 30 mM NADP (FIG. 2B).

Example 6

NADP-Producing Activity of Various Cell Preparations

Various cell preparations were tested for the NADP-producing activity as described in (2) Assay for NADP-producing activity in "Materials and Methods". The results are shown in Table 3 below.

TABLE 3

NADP-producing activity of various cell preparations

| Cell preparation | NADP-producing activity (μmol/g cells/hour) |
| --- | --- |
| Intact cells | 93.5 |
| Homogenate of intact cells (p) | 1530 |
| Acetone-treated cells | 642 |
| Homogenate of acetone-treated cells | 1420 |
| Immobilized cells | 146 |
| Homogenate of immobilized cells (q) | 925 |
| Acetone-treated immobilized cells | 672 |
| Homogenate of acetone-treated immobilized cells | 843 |

The NADP-producing activity of the cell homogenate was 1,530 μmol/g cells/hour. This is defined as "p". On the other hand, the NADP-producing activity of the homogenate of the immobilized cells was 925 μmol/g cells/hour. This is defined as "q". This means that about 60% [(q/p)×100] of the NADP-producing activity initially present in the intact cells was incorporated into the polyacrylamide gel. It should also be noted that the activity of the homogenate of the acetone-treated immobilized cells (843 μmol/g cells/hour) was higher than that of the acetone-treated immobilized cells (672 μmol/g cells/hour). This suggests that the polyacrylamide gel matrix may hinder the transfer of substrates and/or products.

The acetone-treated immobilized cells used here were those obtained in Example 4. The immobilized cells without acetone treatment were the cells before acetone treatment in Example 4. The acetone-treated cells not immobilized on polyacrylamide were obtained by washing cells before acrylamide treatment in ice-cold 5.0 mM Tris-HCl buffer (pH 7.0) and collecting them, followed by acetone treatment as described in Example 4.

Example 7

Functions of Ppnk in the Immobilized Cells

Functions of Ppnk in the acetone-treated immobilized cells obtained in Example 4 were evaluated and compared with those in the non-immobilized acetone-treated cells by the method described in (2) Assay for NADP-producing activity in "Materials and Methods" unless otherwise indicated below.

(1) Effect of Immobilization

A heat treatment at 60° C. for 10 minutes was required to deactivate 50% of the NADP-producing activity of Ppnk in the acetone-treated immobilized cells. While, a treatment at 50° C. sufficed to deactivate 50% of the activity of Ppnk in the non-immobilized acetone-treated cells (FIG. 3A). This shows that the thermostability of Ppnk is enhanced by immobilization into a polyacrylamide gel matrix. The optimal temperature for the NADP-producing activity of Ppnk transferred from 50° C. to 55° C. by immobilization (FIG. 3B).

(2) Effect of pH

The optimal pH for Ppnk-mediated NADP production in the acetone-treated immobilized cells was 7.0, which was somewhat higher than the optimal pH 6.5 in non-immobilized acetone-treated cells (FIG. 3C).

(3) Stability after Use

The acetone-treated immobilized cells were repeatedly used in the NADP-producing reaction assay to compare the stability of the NADP-producing activity of Ppnk after use with that of Ppnk in the non-immobilized acetone-treated cells (FIG. 3D) under the same conditions. The Ppnk activity in the non-immobilized cells was wholly lost after 5 repeated runs. However, the activity in the immobilized cells was unchanged from the start of the assay. The half-life of the Ppnk activity in the acetone-treated immobilized cells was estimated as 75 days or more.

Example 8

Production of NADP by Immobilized Cells

The acetone-treated immobilized cells obtained by treating the immobilized cells with acetone which exerts NAD$^+$ kinase activity from the cells entrapped in acrylamide in Example 4 were used to examine conditions for producing NADP by such cells (FIG. 4A, B, C, D) according to the method described in (2) Assay for NADP-producing activity in "Materials and Methods" unless otherwise indicated below.

(1) Concentration of Metaphosphoric Acid

The NADP-producing activity of Ppnk in the acetone-treated immobilized cells increased with the concentration of metaphosphoric acid at low levels, and reached a plateau at 100 mg/ml, and then gradually decreased (FIG. 4A). In the case of ATP, a similar activity-substrate concentration relationship was observed and the NADP-producing activity reached the maximum level at 150 mM ATP. [ATP]:[Mg$^{2+}$]=3:2 (FIG. 4B).

(2) NAD Levels

The NADP-producing activity of Ppnk in the acetone-treated immobilized' cells increased with the amount of NAD (FIG. 4C). However, the activity was not determined at NAD levels higher than 50 mM.

(3) Metal Ion Levels $Mg^{2+}$ was the most effective among the metal ions reported to be effective for the polyphosphate-dependent NAD kinase activity of Ppnk ($Mg^{2+}$, $Mn^{2+}$, and $Ca^{2+}$[7]. The highest activity was obtained at 100 mM $Mg^{2+}$ in the presence of 100 mg/ml metaphosphoric acid and 50 mM NAD (FIG. 4D). $Mn^{2+}$ and $Ca^{2+}$ form precipitates at concentrations above 5.0 mM.

Example 9

Examination of Reaction Conditions for Synthesizing $NADP^+$ Using *M. Tuberculosis* Recombinant Ppnk Protein Both the *M. tuberculosis* recombinant Ppnk protein obtained in Example 3 and the acetone-treated immobilized cells showing $NAD^+$ kinase activity from the cells entrapped in acrylamide obtained in Example 4 were used to further examine optimization of various reaction conditions for $NADP^+$ synthesis. The results show that optimal reaction conditions include the pH and polyphosphate and metal ion levels shown in the table below.

TABLE 4

|  | Immobilized enzyme | Purified enzyme (soluble) |
| --- | --- | --- |
| Working pH range | pH 6-8 | pH 5.5-8 |
| Level of metaphosphoric acid (and metaphosphates) | 2-15% (w/v) | 2-15% (w/v) |
| Metal ion level | 50-150 mM $MgCl_2$ | 50-150 mM $MgCl_2$ |

Example 10

$NAD^+$ Kinase Activity Under Optimal Conditions of the Present Invention

The acetone-treated immobilized cells (10 units) of Example 4 were incubated in an optimal reaction mixture [50 mM NAD, 100 mg/ml metaphosphoric acid (or 150 mM ATP (FIG. 5B)), 100 mM $MgCl_2$, and 100 mM Tris-HCl (pH 7.0)]. After completion of the reaction, the amount of $NADP^+$ synthesized was analyzed by an enzymatic assay using an $NADP^+$-specific glucose-6-phosphate dehydrogenase (from yeast available from Oriental Yeast, Co., Ltd.). The results show that a maximum yield of 16 mM NADP was produced (14 g/l) (FIG. 5A). However, the immobilized SK45 cells produced no or very little NADP under the same conditions (FIG. 5A, B).

The low conversion efficiency from NAD into NADP (about 30%) may be attributed, but not limited, to the inhibitory effect of the produced NADP (FIG. 2B) and/or the limitation of diffusion of the product or substrate by the polyacrylamide gel matrix because the decomposition of NAD and NADP by the acetone-treated immobilized cells is negligible. Removal of NADP from the reaction system results in an increase in transfer efficiency.

The amount of NADP produced by the immobilized SK27 cells (16 mM, 14 g/l) (FIG. 5A) was about 8 times higher than the amount of NADP obtained from the immobilized *B. ammoniagenes* cells (2.0 mM, 1.7 g/l) [4]. This value was approximately comparable to the amount of NADP produced by using ATP (150 mM) (FIG. 5B) in place of metaphosphoric acid as a substrate.

The NADP-producing activity of purified Ppnk protein was also tested under optimal conditions to show that it was 30 mM, 26 g whether NADP or ATP was used. The amount of $NADP^+$ produced after completion of each recombinant $NAD^+$; kinase reaction is shown in the table below.

TABLE 5

| Ppnk protein | ATP | Metaphosphoric acid |
| --- | --- | --- |
| M. tuberculosis Ppnk (purified) | 30 mM | 30 mM |
| M. tuberculosis PpnK (immobilized) (Control) | 16 mM | 16 mM |
| Brevibacterium ammoniagenes (immobilized) |  | 2 mM*) |

Table 5 above shows that *M. tuberculosis* Ppnk of the present invention (as purified protein and/or in the immobilized recombinant cells) is very efficient as compared with conventional ATP-dependent NAD kinases [4].

Example 11

Analysis of Reaction Products

Purified Ppnk and immobilized cells were used for a reaction of producing NADP in the presence of ATP or metaphosphoric acid to examine changes of components before and after the reaction.

Specifically, an NADP-producing reaction was performed as described in (2) Assay for NADP-producing activity in "Materials and Methods" using the purified Ppnk protein and the immobilized cells in the presence of 50 mg/ml metaphosphoric acid or 50 mM ATP. At the end of the reaction for 24 hours, the reaction solution was diluted 50-fold with 50 mM Tris-acetate buffer (pH 7.5) and the dilution (30 µl) was applied onto a TSK-GEL 80TS column (0.46 cm in diameter× 15 cm in height) (Tosoh, Tokyo, Japan). Then, the nucleotide fraction adsorbed to the column was separated by gradient elution of 0-10% methanol. The flow rate was adjusted to 0.7 ml/min. The extracted nucleotide fraction was determined by measuring the absorbance at 260 nm.

The results show that the mixture after the reaction using ATP and the purified Ppnk protein contained unreacted ATP and NAD in addition to the reaction products NADP and ADP (FIG. 6B). When ATP and the immobilized cells were used, the mixture after the reaction further contained a decomposition product of ADP, AMP in addition to NADP and ADP and unreacted ATP and NAD (FIG. 6C). Thin-layer chromatography further showed that adenosine was formed (data not shown). When metaphosphoric acid was used in place of ATP, however, the mixture after the reaction contained only NADP and unreacted NAD in either event the purified Ppnk (FIG. 6E) or the immobilized cells (FIG. 6F) was used.

Example 12

Phosphate-Donating Substrates in Metaphosphoric Acid

Metaphosphoric acid is a mixture of cyclic and/or linear polyphosphates having various degrees of polymerization. To identify essential phosphate-donating substrates for the polyphosphate-dependent NAD kinase activity of Ppnk, polyphosphates in metaphosphoric acid were separated on an ion exchange column as follows.

Metaphosphoric acid (10%, 60 ml, pH 7.0) was dialyzed against 3,000 ml of water using a Seamless Cellulose Tube (cut-off: 12,000-14,000 Da) (Viskase Sales Corp, Chicago, Ill.) at 25° C. for 24 hours. The dialysate (2,900 ml) was loaded onto a Dowex 1×2 (Cl⁻, 200-400 meshes) column (3.0×6.0 cm) (Muromachi Chemicals Ltd., Tokyo, Japan). Then, adsorbed polyphosphates were eluted with a linear gradient of LiCl (600 ml, 0-1.0M, pH 2.0) to give a 6.0 ml fraction every 6 minutes. A part of each fraction (0.10 ml) was used to assay the polyphosphate dependent NAD kinase activity of Ppnk as described above. FIG. 7 shows elution patterns of phosphate donors in metaphosphoric acid on Dowex 1×2 column. Solid circles represent phosphate-donating activity, open circles represent acid-labile phosphate, and the dotted line represents the concentration of LiCl. The amount of NADP produced in one minute was defined as phosphate-donating activity. Acid-labile phosphate in each fraction was estimated by determining inorganic orthophosphoric acid released from metaphosphoric acid after the eluate was boiled in 1N HCl for 7 minutes [12].

As shown in FIG. 7, phosphate-donating activity was detected in all the fractions eluted at concentrations higher than 0.20M LiCl (fraction # 25-80 in FIG. 8), and about 84% of the phosphate-donating activity was recovered from the dialysate when metaphosphoric acid was dialyzed against water. This means that most substrates for the enzyme mostly consist of polyphosphates having a molecular weight less than about 12,000-14,000 Da. In FIG. 7, four peaks (fractions 32-40, fractions 44-52, fractions 56-60, and fractions 64-72) are observed, suggesting that metaphosphoric acid has at least four phosphate-donating substrates for the polyphosphate-dependent NAD kinase.

EFFECTS OF THE INVENTION

Industrial applications of microbial enzymes have been so far limited to the catalysis of decompositions and simple transformation reactions. The enzymes have not been widely applied to synthetic reactions demanding energy (ATP) supply on a commercial scale. One limitation of the development of economically feasible ATP-demanding processes is the lack of an appropriate system for (re)generating and/or recycling ATP.

Therefore, it is essential to construct a system for (re)generating ATP not only for economical utilization of the enzyme but also for the economy of processes and the efficiency of the reaction. For this purpose, various approaches for (re)generating ATP have been proposed including chemical synthesis, whole cell, cell organeller or sub-cellular systems, and cell-free systems [13]. However, the technical and economical feasibility of these approaches as ATP-regenerating systems has been unknown except for the use of sub-celluar systems (glycolytic systems) despite the recent great development in technology [14][15].

The production system using polyphosphates as phosphate donors provided by the present invention offers an alternative to systems using ATP-dependent NAD⁺ kinases for producing useful compounds for the following reasons.

1. Polyphosphates used in the processes of the present invention can be purchased at low prices. Accordingly, they can be used in a sufficient amount as substrates for polyphosphate-dependent NAD kinases (FIG. 7), so that the production system of the present invention is very economical.

2. According to the production system of the present invention, the product (NADP) can be easily isolated because no decomposition products of ATP (ADP, AMP) are contained after the reaction (FIG. 6).

3. Various enzymes using polyphosphates as energy sources are found in microorganisms [6]. Some of them can be readily applied to biosynthetic systems for producing useful biochemical compounds (e.g. producing glucose-6-phosphate from glucose and metaphosphate on an immobilized *Achromobacter butyri* cell column [11]). Therefore, the NADP⁺ production reaction of the present invention can be further combined with e.g. a glucose-6-phosphate production reaction and NADP⁺-dependent glucose-6-phosphate dehydrogenase (e.g. from yeast available from Oriental Yeast, Co., Ltd.) to readily synthesize NADPH from glucose, polyphosphate and NAD⁺ at low cost as shown by the formulae below.

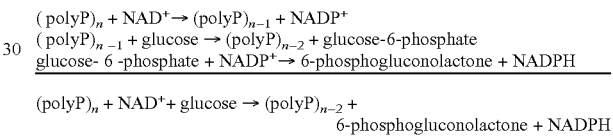

4. Genetic engineering and protein engineering techniques well known to those skilled in the art can be used to convert known ATP-dependent NAD⁺ kinases into polyphosphate-dependent kinases. Recent findings show that the ATP-dependent NAD kinase in *E. coli* also has polyphosphate-dependent NAD kinase activity but at a very low level. The nucleotide sequences of the ATP-dependent NAD kinases from *E. coli* and the yeast *Saccharomyces cerevisiae* [17] are similar to the sequence of the polyphosphate/ATP-dependent NAD kinase from *M. tuberculosis* H37Rv of the present invention (SEQ ID NO: 1).

Considering that biochemical energy carriers are derived from polyphosphates [18], the similarity of the nucleotide sequences suggests that ATP-dependent NAD kinases were evolved from polyphosphate-dependent NAD kinases probably by accumulation of point mutations. In fact, NAD kinases using polyphosphates in place of ATP as substrates are being successfully prepared by random mutation. Various ATP-dependent NAD kinases from *Mycobacteria* or other genera can be converted into polyphosphate-dependent NAD kinases by mutation and applied to the present invention.

The invention claimed is:

1. A process for preparing nicotinamide adenine dinucleotide phosphate (NADP) in vitro comprising performing phosphorylation using a polyphosphoric acid or a salt thereof and nicotinamide adenine dinucleotide ($NAD^+$) as substrates in the presence of a polyphosphate-dependent $NAD^+$ kinase from a *Mycobacterium*, wherein the reaction solution contains 5-15% by weight of the polyphosphoric acid or a salt thereof, 8-50 mM of $NAD^+$ and 5-150 mM of a divalent metal ion, and a pH of the reaction solution is in a range of 6-7, and
wherein the $NAD^+$ kinase is
a polypeptide comprising the amino acid sequence of SEQ ID NO:1, and
having an optimal pH of 5.5-6.5.

2. The process of claim 1 wherein the NAD+ kinase from the *Mycobacterium* is NAD+ kinase from *M. tuberculosis* (*Mycobacterium tuberculosis*).

3. The process of claim 1 wherein the NAD+ kinase from the *Mycobacterium* is a solubilized or immobilized protein or is a protein expressed in immobilized cells.

4. The process of claim 1 wherein the polyphosphoric acid or a salt thereof is selected from the group consisting of metaphosphoric acid, hexametaphosphoric acid and salts thereof and mixtures thereof.

5. The process of claim 1 wherein the reaction solution contains 50-100 mM of a divalent metal ion.

6. The process of claim 1 wherein the divalent metal ion is selected from magnesium ion or manganese ion.

7. The process of claim 1 wherein the divalent metal ion is within a chloride, sulfate or nitrate salt.

8. The process of claim 1 wherein the reaction solution contains 10-15% by weight of a polyphosphoric acid or salt thereof.

* * * * *

SEQUENCE LISTING

<160> NUMBER OF SEQ ID NOS: 4

<210> SEQ ID NO 1
<211> LENGTH: 307
<212> TYPE: PRT
<213> ORGANISM: Mycobacteria tuberculosis H37Rv

<400> SEQUENCE: 1

```
Met Thr Ala His Arg Ser Val Leu Leu Val Val His Thr Gly Arg
 1               5                  10                  15
Asp Glu Ala Thr Glu Thr Ala Arg Arg Val Glu Lys Val Leu Gly
                20                  25                  30
Asp Asn Lys Ile Ala Leu Arg Val Leu Ser Ala Glu Ala Val Asp
                35                  40                  45
Arg Gly Ser Leu His Leu Ala Pro Asp Met Arg Ala Met Gly
                50                  55                  60
Val Glu Ile Glu Val Val Asp Ala Asp Gln His Ala Ala Asp Gly
                65                  70                  75
Cys Glu Leu Val Leu Val Leu Gly Gly Asp Gly Thr Phe Leu Arg
                80                  85                  90
Ala Ala Glu Leu Ala Arg Asn Ala Ser Ile Pro Val Leu Gly Val
                95                  100                 105
Asn Leu Gly Arg Ile Gly Phe Leu Ala Glu Ala Glu Ala Glu Ala
                110                 115                 120
Ile Asp Ala Val Leu Glu His Val Val Ala Gln Asp Tyr Arg Val
                125                 130                 135
Glu Asp Arg Leu Thr Leu Asp Val Val Arg Gln Gly Gly Arg
                140                 145                 150
Ile Val Asn Arg Gly Trp Ala Leu Asn Glu Val Ser Leu Glu Lys
                155                 160                 165
Gly Pro Arg Leu Gly Val Leu Gly Val Val Glu Ile Asp Gly
                170                 175                 180
Arg Pro Val Ser Ala Phe Gly Cys Asp Gly Val Leu Val Ser Thr
                185                 190                 195
Pro Thr Gly Ser Thr Ala Tyr Ala Phe Ser Ala Gly Gly Pro Val
                200                 205                 210
Leu Trp Pro Asp Leu Glu Ala Ile Leu Val Val Pro Asn Asn Ala
                215                 220                 225
His Ala Leu Phe Gly Arg Pro Met Val Thr Ser Pro Glu Ala Thr
                230                 235                 240
Ile Ala Ile Glu Ile Glu Ala Asp Gly His Asp Ala Leu Val Phe
                245                 250                 255
Cys Asp Gly Arg Arg Glu Met Leu Ile Pro Ala Gly Ser Arg Leu
                260                 265                 270
Glu Val Thr Arg Cys Val Thr Ser Val Lys Trp Ala Arg Leu Asp
                275                 280                 285
Ser Ala Pro Phe Thr Asp Arg Leu Val Arg Lys Phe Arg Leu Pro
                290                 295                 300
Val Thr Gly Trp Arg Gly Lys
                305     307
```

<210> SEQ ID NO 2
<211> LENGTH: 921
<212> TYPE: DNA
<213> ORGANISM: Mycobacteria tuberculosis H37Rv

<400> SEQUENCE: 2

```
atgaccgctc atcgcagtgt tctgctggtc gtccacaccg ggcgcgacga agccaccgag    60
accgcacggc gcgtagaaaa agtattgggc gacaataaaa ttgcgcttcg cgtgctctcg   120
gccgaagcag tcgaccgagg gtcgttgcat ctggctcccg acgacatgcg ggccatgggc   180
```

```
-continued gtcgagatcg aggtggttga cgcggaccag cacgcagccg acggctgcga actggtgctg      240
gttttgggcg gcgatggcac cttttttgcgg gcagccgagc tggcccgcaa cgccagcatt     300
ccggtgttgg gcgtcaatct gggccgcatc ggcttttttgg ccgaggccga ggcggaggca     360
atcgacgcgg tgctcgagca tgttgtcgca caggattacc gggtggaaga ccgcttgact      420
ctggatgtcg tggtgcgcca gggcgggcgc atcgtcaacc ggggttgggc gctcaacgaa      480
gtcagtctgg aaaagggccc gaggctcggc gtgcttgggg tggtcgtgga aattgacggt     540
cggccggtgt cggcgtttgg ctgcgacggg gtgttggtgt ccacgccgac cggatcaacc     600
gcctatgcat tctcggcggg aggcccggtg ctgtggcccg acctcgaagc gatcctggtg    660
gtccccaaca acgctcacgc gctgtttggc cggccgatgg tcaccagccc cgaagccacc    720
atcgccatcg aaatagaggc cgacgggcat gacgccttgg tgttctgcga cggtcgccgc   780
gaaatgctga taccggccgg cagcagactc gaggtcaccc gctgtgtcac gtccgtcaaa   840
tgggcacggc tggacagtgc gccattcacc gaccggctgg tgcgcaagtt ccggttgccg   900
gtgaccggtt ggcgcggaaa g                                               921

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer for
      PCR amplification

<400> SEQUENCE: 3
cccatatgac cgctcatcgc agtgttctg                                        29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: primer for
      PCR amplification

<400> SEQUENCE: 4
cggatcccta ctttccgcgc caaccggtc                                        29
```